(12) United States Patent
Yonezawa

(10) Patent No.: US 8,951,526 B2
(45) Date of Patent: Feb. 10, 2015

(54) ANTIBODY AGAINST MUCIN 1 (MUC1) PROTEIN AND USE OF SAME

(75) Inventor: Suguru Yonezawa, Kagoshima (JP)

(73) Assignee: Kagoshima University, Kagoshima-Shi, Kagoshima (JP)

( * ) Notice: Subject to any disclaimer, the term of this patent is extended or adjusted under 35 U.S.C. 154(b) by 0 days.

(21) Appl. No.: 13/577,841

(22) PCT Filed: Feb. 10, 2011

(86) PCT No.: PCT/JP2011/052893
§ 371 (c)(1),
(2), (4) Date: Aug. 8, 2012

(87) PCT Pub. No.: WO2011/099566
PCT Pub. Date: Aug. 18, 2011

(65) Prior Publication Data
US 2013/0045490 A1    Feb. 21, 2013

(30) Foreign Application Priority Data

Feb. 12, 2010  (JP) ................................. 2010-028729
Apr. 21, 2010  (JP) ................................. 2010-097922

(51) Int. Cl.
*C07K 16/30*   (2006.01)
*G01N 33/574*  (2006.01)
*C07K 14/47*   (2006.01)

(52) U.S. Cl.
CPC .......... *C07K 16/3092* (2013.01); *C07K 14/4727* (2013.01); *G01N 2333/4725* (2013.01); *C07K 2317/34* (2013.01)
USPC .................. 424/156.1; 424/138.1; 530/391.3; 530/388.85; 435/7.23

(58) Field of Classification Search
None
See application file for complete search history.

(56) References Cited

U.S. PATENT DOCUMENTS

2005/0282744 A1    12/2005 Hollingsworth et al.

FOREIGN PATENT DOCUMENTS

EP          1983003     * 10/2008

OTHER PUBLICATIONS

Hamann, Bioconjugate Chemistry, vol. 16, p. 346-353, 2005.*
Polyak, Blood, vol. 99, No. 9, p. 3256-3262, 2002.*
Munodzana, Infection and Immunity, vol. 66 No. 6, p. 2619-2624, 1998.*
Harris et al., Biotechnology, vol. 11, p. 1293-1297, 1993.*
Rudikoff et al, Proc. Natl. Acad. Sci. USA, 79(6):1979-1983, Mar. 1982.*
Colman P. M., Research in Immunology, 145:33-36, 1994.*
Pemberton, Lucy, et al., Antibodies to the cytoplasmic domain of the MUCI mucin show conservation throughout mammals., Biochem. Biophys. Res. Commun., 1992, vol. 185, No. 1, p. 167-175.
Croce, M. V., et al., MUCI cytoplasmic tail detection using CT33 polyclonal and CT2 monoclonal antibodies in breast and colorectal tissue., Histol. Histopathol., 2006, vol. 21, p. 849-855.
Croce, Maria V., et al., Patterns of MUC1 tissue expression defined by an anti-MUC1 cytoplasmic tail monoclonal antibody in breast cancer., J. Histochem. Cytochem., 2003, vol. 51, No. 6, p. 781-788.
Baldus, Stephan E., et al., Correlation of the immunohistochemical reactivity of mucin peptide cores MUC1 and MUC2 with the histopathological subtype and prognosis of gastric carcinomas., Int. J. Cancer., 1998, vol. 79, p. 133-138.
Gendler, Sandra J., et al., Molecular cloning and expression of human tumor-associated polymorphic epithelial mucin., J. Biol. Chem., 1990, vol. 265, No. 25, p. 15286-15293.
Sakamoto, Hideie, et al., Mucin antigen expression in gastric carcinomas of young and old adults., Hum. Pathol., 1997, vol. 28, No. 9, p. 1056-1065.
Lee, Hye Seung, et al., MUC1, MUC2, MUC5AC, and MUC6 expressions in gastric carcinomas: their roles as prognostic indicators., Cancer, 2001, vol. 92, No. 6, p. 1427-1434.
Kohlgraf Karl G. et al., Contribution of the MUC1 tandem repeat and cytoplasmic tail to invasive and metastatic properties of a pancreatic cancer cell line., Cancer Res., 2003, vol. 63, p. 5011-5020.
Quin, Rachel, et al., Phosphorylation of the cytoplasmic domain of the MUC1 mucin correlates with changes in cell-cell adhesion., Int. J. Cancer., 2000, vol. 87, p. 499-506.
Meerzaman, Daoud, et al., Construction and characterization of a chimeric receptor containing the cytoplasmic domain of MUC1 mucin., Am. J. Physiol. Lung. Cell. Mol. Physiol., 2000, vol. 278, p. L625-L629.
Office Action, dated Apr. 15, 2014, cited in corresponding Japanese patent application No. 2010-097922.

* cited by examiner

Primary Examiner — Hong Sang
Assistant Examiner — Michael D Allen
(74) Attorney, Agent, or Firm — Lucas & Mercanti, LLP

(57) ABSTRACT

The present invention provides means and a method assuring the effectiveness of early diagnosis of cancers including gastric cancers. Specifically, the present invention provides an antibody, which is prepared using, as an antigen, (a) a peptide comprising at least contiguous amino acids at positions 69 to 75 in the amino acid sequence of SEQ ID NO: 2, or (b) a peptide consisting of an amino acid sequence in which one or several amino acids are deleted, substituted or added in at least contiguous amino acids at positions 69 to 75 in the amino acid sequence of SEQ ID NO: 2, and having the antigenicity of human MUC1 protein, and which is reactive with human mucin 1 (MUC1) protein.

8 Claims, 18 Drawing Sheets
(13 of 18 Drawing Sheet(s) Filed in Color)

FIG.2

Amino acid sequence of human MUC1 protein (901-1255)

```
 901  APDTRPAPGS TAPPAHGVTS APDTRPAPGS TAPPAHGVTS APDNRPALGS TAPPVHNVTS
                            └──────────┘
                            Epitope – No.1
 961  ASGSASGSAS TLVHNGTSAR ATTPASKST  PFSIPSHHSD TPTTLASHST KTDASSTHHS
                              └───────┘      └────────┘  └────────┘ └──────
                              Epitope        Epitope      Epitope   Epitope
                              – No.2         – No.3       – No.6    – No.4
1021  SVPPLTSSNH STSPQLSTGV SFFFLSFHIS NLQFNSSLED PSTDYQELQ RDISEMFLQI
            └───────┘                        └──────────┘
            Epitope                          Epitope
            – No.5                           – No.6
1081  YKQGGFLGLS NIKFRPGSVV VQLTLAFREG TINVHDVETQ FNQYKTEAAS RYNLTISDVS
            └───────────────────────┘  └────────┘ └────────┘
            Cleavage site                         Epitope
                                                  – No.7
1141  VSDVPFPFSA QSGAGVPGWG IALLVLVCVL VALAIVYLIA LAVCQRRKN YGQLDIFPAR
                            └─────────────────────────────┘ └────────┘
                            Transmembrane region            Epitope
                                                            – No.8
1201  DTYHPMSEYP TYHTHGRYVP PSSTDRSPYE KVSAGNGGSS LSYTNPAVAA ASANL
                    └────────┘ └────────┘
                    Epitope     Epitope
                    – No.9      – No.10
```

— 45aa sequence
= 19aa common sequence (Cys is added to N-terminus)

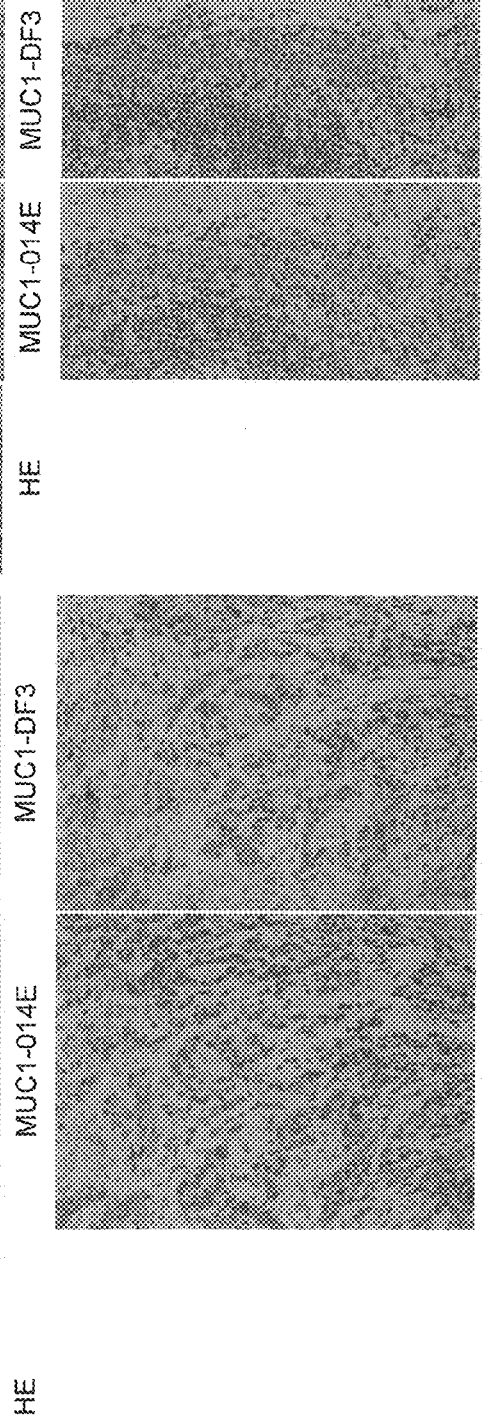
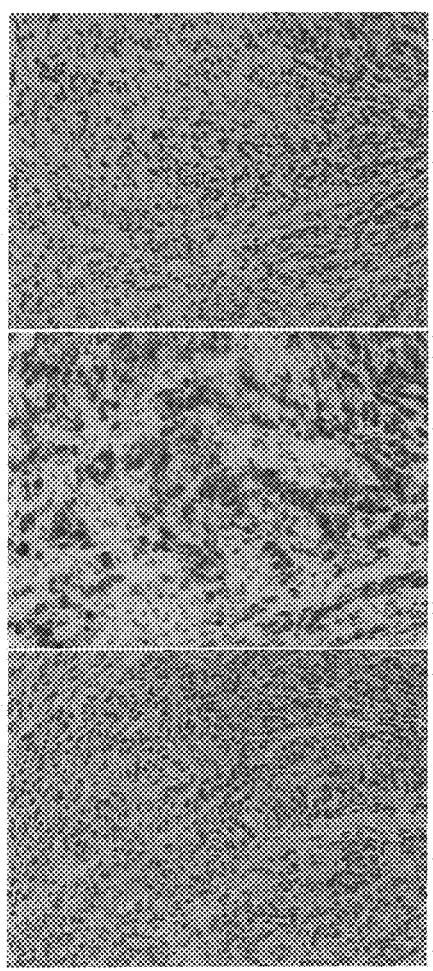
FIG. 12

FIG.15
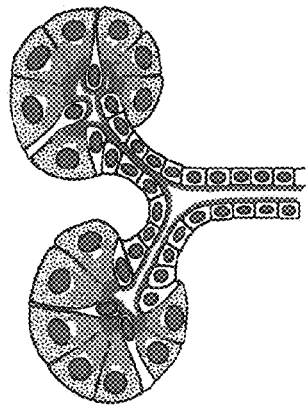
A
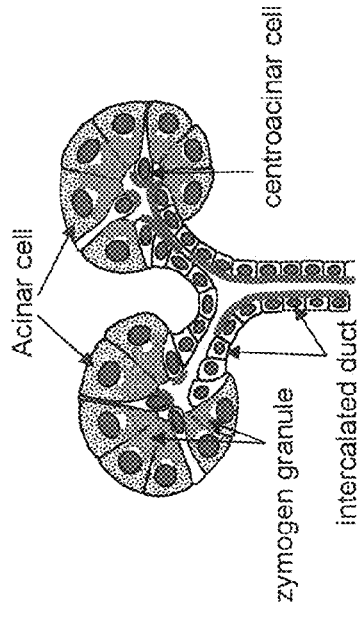
B
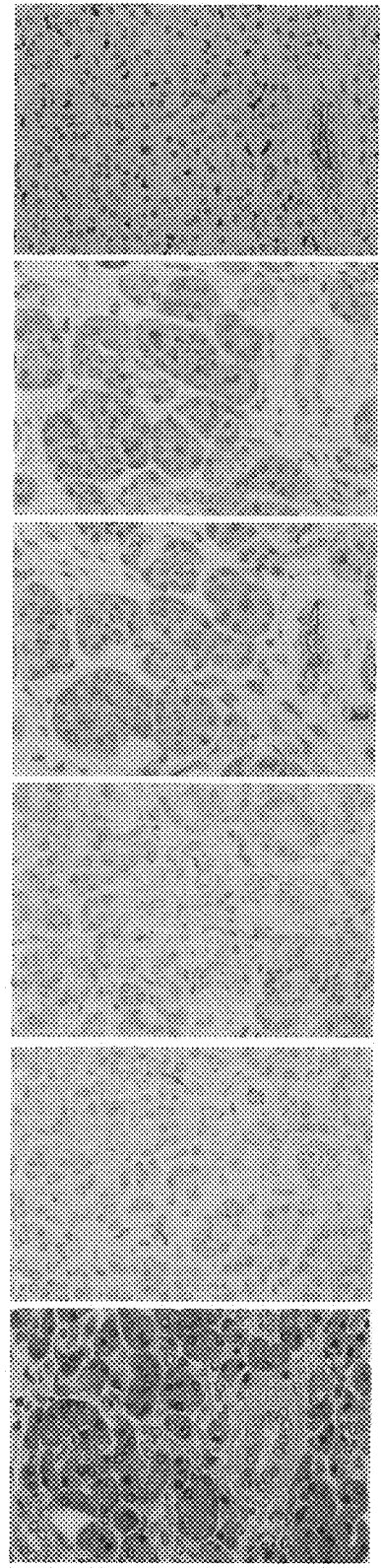

```
SEQUENCE LISTING

<160> NUMBER OF SEQ ID NOS: 28

<210> SEQ ID NO 1
<211> LENGTH: 19
<212> TYPE: PRT
<213> ORGANISM: Artificial
<220> FEATURE:
<223> OTHER INFORMATION: synthetic peptide

<400> SEQUENCE: 1

Arg Tyr Val Pro Pro Ser Ser Thr Asp Arg Ser Pro Tyr Glu Lys Val
1               5                   10                  15

Ser Ala Gly

<210> SEQ ID NO 2
<211> LENGTH: 84
<212> TYPE: PRT
<213> ORGANISM: Artificial
<220> FEATURE:
<223> OTHER INFORMATION: synthetic peptide

<400> SEQUENCE: 2

Gly Val Pro Gly Trp Gly Ile Ala Leu Leu Val Leu Val Cys Val Leu
1               5                   10                  15
```

```
Val Ala Leu Ala Ile Val Tyr Leu Ile Ala Leu Ala Val Cys Gln Cys
             20                  25                  30

Arg Arg Lys Asn Tyr Gly Gln Leu Asp Ile Phe Pro Ala Arg Asp Thr
         35                  40                  45

Tyr His Pro Met Ser Glu Tyr Pro Thr Tyr His Thr His Gly Arg Tyr
     50                  55                  60

Val Pro Pro Ser Ser Thr Asp Arg Ser Pro Tyr Glu Lys Val Ser Ala
65                  70                  75                  80

Gly Asn Gly Gly

<210> SEQ ID NO 3
<211> LENGTH: 1255
<212> TYPE: PRT
<213> ORGANISM: Homo sapiens

<400> SEQUENCE: 3

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
             20                  25                  30

Gly Glu Lys Glu Thr Ser Ala Thr Gln Arg Ser Ser Val Pro Ser Ser
         35                  40                  45

Thr Glu Lys Asn Ala Val Ser Met Thr Ser Ser Val Leu Ser Ser His
     50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300
```

```
Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720
```

```
Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
                755                 760                 765

Gly Ser Thr Ala Pro Pro Ala His Gly Val Thr Ser Ala Pro Asp Thr
                770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
                835                 840                 845

Gly Ser Thr Ala Pro Pro Ala His Gly Val Thr Ser Ala Pro Asp Thr
                850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
                915                 920                 925

Gly Ser Thr Ala Pro Pro Ala His Gly Val Thr Ser Ala Pro Asp Asn
                930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
                980                 985                 990

Ser Ile Pro Ser His His Ser Asp Thr Pro Thr Thr Leu Ala Ser His
                995                 1000                1005

Ser Thr Lys Thr Asp Ala Ser Ser Thr His His Ser Ser Val Pro
                1010                1015                1020

Pro Leu Thr Ser Ser Asn His Ser Thr Ser Pro Gln Leu Ser Thr
                1025                1030                1035

Gly Val Ser Phe Phe Phe Leu Ser Phe His Ile Ser Asn Leu Gln
                1040                1045                1050

Phe Asn Ser Ser Leu Glu Asp Pro Ser Thr Asp Tyr Tyr Gln Glu
                1055                1060                1065

Leu Gln Arg Asp Ile Ser Glu Met Phe Leu Gln Ile Tyr Lys Gln
                1070                1075                1080

Gly Gly Phe Leu Gly Leu Ser Asn Ile Lys Phe Arg Pro Gly Ser
                1085                1090                1095

Val Val Val Gln Leu Thr Leu Ala Phe Arg Glu Gly Thr Ile Asn
                1100                1105                1110

Val His Asp Val Glu Thr Gln Phe Asn Gln Tyr Lys Thr Glu Ala
                1115                1120                1125

Ala Ser Arg Tyr Asn Leu Thr Ile Ser Asp Val Ser Val Ser Asp
```

| | | | | | | | | | |
|---|---|---|---|---|---|---|---|---|---|
| | | 1130 | | | 1135 | | | 1140 | |
| Val | Pro | Phe | Pro | Phe | Ser | Ala | Gln | Ser | Gly | Ala | Gly | Val | Pro | Gly |
| | | 1145 | | | | 1150 | | | | 1155 | | | | |
| Trp | Gly | Ile | Ala | Leu | Leu | Val | Leu | Val | Cys | Val | Leu | Val | Ala | Leu |
| | | 1160 | | | | 1165 | | | | 1170 | | | | |
| Ala | Ile | Val | Tyr | Leu | Ile | Ala | Leu | Ala | Val | Cys | Gln | Cys | Arg | Arg |
| | | 1175 | | | | 1180 | | | | 1185 | | | | |
| Lys | Asn | Tyr | Gly | Gln | Leu | Asp | Ile | Phe | Pro | Ala | Arg | Asp | Thr | Tyr |
| | | 1190 | | | | 1195 | | | | 1200 | | | | |
| His | Pro | Met | Ser | Glu | Tyr | Pro | Thr | Tyr | His | Thr | His | Gly | Arg | Tyr |
| | | 1205 | | | | 1210 | | | | 1215 | | | | |
| Val | Pro | Pro | Ser | Ser | Thr | Asp | Arg | Ser | Pro | Tyr | Glu | Lys | Val | Ser |
| | | 1220 | | | | 1225 | | | | 1230 | | | | |
| Ala | Gly | Asn | Gly | Gly | Ser | Ser | Leu | Ser | Tyr | Thr | Asn | Pro | Ala | Val |
| | | 1235 | | | | 1240 | | | | 1245 | | | | |
| Ala | Ala | Ala | Ser | Ala | Asn | Leu | | | | | | | | |
| | | 1250 | | | | 1255 | | | | | | | | |

<210> SEQ ID NO 4
<211> LENGTH: 3768
<212> TYPE: DNA
<213> ORGANISM: Homo sapiens

<400> SEQUENCE: 4

```
atgacaccgg gcacccagtc tcctttcttc ctgctgctgc tcctcacagt gcttacagtt      60
gttacaggtt ctggtcatgc aagctctacc ccaggtggag aaaaggagac ttcggctacc     120
cagagaagtt cagtgcccag ctctactgag aagaatgctg tgagtatgac cagcagcgta     180
ctctccagcc acagcccggg ttcaggctcc tccaccactc agggacagga tgtcactctg     240
gccccggcca cggaaccagc ttcaggttca gctgccacct ggggacagga tgtcacctcg     300
gtccagtca ccaggccagc cctgggctcc accaccccgc agcccacga tgtcacctca      360
gccccggaca caagccagc cccgggctcc accgcccccc agcccacgg tgtcacctcg       420
gccccggaca ccaggccggc cccgggctcc accgcccccc agcccacgg tgtcacctcg      480
gccccggaca ccaggccggc cccgggctcc accgcccccc agcccacgg tgtcacctcg      540
gccccggaca ccaggccggc cccgggctcc accgcccccc agcccacgg tgtcacctcg      600
gccccggaca ccaggccggc cccgggctcc accgcccccc agcccacgg tgtcacctcg      660
gccccggaca ccaggccggc cccgggctcc accgcccccc agcccacgg tgtcacctcg      720
gccccggaca ccaggccggc cccgggctcc accgcccccc agcccacgg tgtcacctcg      780
gccccggaca ccaggccggc cccgggctcc accgcccccc agcccacgg tgtcacctcg      840
gccccggaca ccaggccggc cccgggctcc accgcccccc agcccacgg tgtcacctcg      900
gccccggaca ccaggccggc cccgggctcc accgcccccc agcccacgg tgtcacctcg      960
gccccggaca ccaggccggc cccgggctcc accgcccccc agcccacgg tgtcacctcg     1020
gccccggaca ccaggccggc cccgggctcc accgcccccc agcccacgg tgtcacctcg     1080
gccccggaca ccaggccggc cccgggctcc accgcccccc agcccacgg tgtcacctcg     1140
gccccggaca ccaggccggc cccgggctcc accgcccccc agcccacgg tgtcacctcg     1200
gccccggaca ccaggccggc cccgggctcc accgcccccc agcccacgg tgtcacctcg     1260
gccccggaca ccaggccggc cccgggctcc accgcccccc agcccacgg tgtcacctcg     1320
gccccggaca ccaggccggc cccgggctcc accgcccccc agcccacgg tgtcacctcg     1380
```

```
gccccggaca ccaggccggc cccgggctcc accgccccc cagcccacgg tgtcacctcg    1440
gccccggaca ccaggccggc cccgggctcc accgccccc cagcccacgg tgtcacctcg    1500
gccccggaca ccaggccggc cccgggctcc accgccccc cagcccacgg tgtcacctcg    1560
gccccggaca ccaggccggc cccgggctcc accgccccc cagcccacgg tgtcacctcg    1620
gccccggaca ccaggccggc cccgggctcc accgccccc cagcccacgg tgtcacctcg    1680
gccccggaca ccaggccggc cccgggctcc accgccccc cagcccacgg tgtcacctcg    1740
gccccggaca ccaggccggc cccgggctcc accgccccc cagcccacgg tgtcacctcg    1800
gccccggaca ccaggccggc cccgggctcc accgccccc cagcccacgg tgtcacctcg    1860
gccccggaca ccaggccggc cccgggctcc accgccccc cagcccacgg tgtcacctcg    1920
gccccggaca ccaggccggc cccgggctcc accgccccc cagcccacgg tgtcacctcg    1980
gccccggaca ccaggccggc cccgggctcc accgccccc cagcccacgg tgtcacctcg    2040
gccccggaca ccaggccggc cccgggctcc accgccccc cagcccacgg tgtcacctcg    2100
gccccggaca ccaggccggc cccgggctcc accgccccc cagcccacgg tgtcacctcg    2160
gccccggaca ccaggccggc cccgggctcc accgccccc cagcccacgg tgtcacctcg    2220
gccccggaca ccaggccggc cccgggctcc accgccccc cagcccacgg tgtcacctcg    2280
gccccggaca ccaggccggc cccgggctcc accgccccc cagcccacgg tgtcacctcg    2340
gccccggaca ccaggccggc cccgggctcc accgccccc cagcccacgg tgtcacctcg    2400
gccccggaca ccaggccggc cccgggctcc accgccccc cagcccacgg tgtcacctcg    2460
gccccggaca ccaggccggc cccgggctcc accgccccc cagcccacgg tgtcacctcg    2520
gccccggaca ccaggccggc cccgggctcc accgccccc cagcccacgg tgtcacctcg    2580
gccccggaca ccaggccggc cccgggctcc accgccccc cagcccacgg tgtcacctcg    2640
gccccggaca ccaggccggc cccgggctcc accgccccc cagcccacgg tgtcacctcg    2700
gccccggaca ccaggccggc cccgggctcc accgccccc cagcccacgg tgtcacctcg    2760
gccccggaca ccaggccggc cccgggctcc accgccccc cagcccatgg tgtcacctcg    2820
gccccggaca acaggcccgc cttgggctcc accgcccctc cagtccacaa tgtcacctcg    2880
gcctcaggct ctgcatcagg ctcagcttct actctggtgc acaacggcac ctctgccagg    2940
gctaccacaa ccccagccag caagagcact ccattctcaa ttcccagcca ccactctgat    3000
actcctacca cccttgccag ccatagcacc aagactgatg ccagtagcac tcaccatagc    3060
tcggtacctc ctctcacctc ctccaatcac agcacttctc cccagttgtc tactggggtc    3120
tctttctttt tcctgtcttt tcacatttca aacctccagt ttaattcctc tctggaagat    3180
cccagcaccg actactacca agagctgcag agagacattt ctgaaatgtt tttgcagatt    3240
tataaacaag ggggttttct gggcctctcc aatattaagt tcaggccagg atctgtggtg    3300
gtacaattga ctctggcctt ccgagaaggt accatcaatg tccacgacgt ggagacacag    3360
ttcaatcagt ataaaacgga agcagcctct cgatataacc tgacgatctc agacgtcagc    3420
gtgagtgatg tgccatttcc tttctctgcc cagtctgggg ctggggtgcc aggctgggc     3480 atcgcgctgc tggtgctggt ctgtgttctg gttgcgctgg ccattgtcta tctcattgcc    3540
ttggctgtct gtcagtgccg ccgaaagaac tacgggcagc tggacatctt ccagcccgg    3600 gatacctacc atcctatgag cgagtacccc acctaccaca cccatgggcg ctatgtgccc    3660
cctagcagta ccgatcgtag cccctatgag aaggtttctg caggtaacgg tggcagcagc    3720
```
ctctcttaca caaacccagc agtggcagcc gcttctgcca acttgtag    3768

<210> SEQ ID NO 5
<211> LENGTH: 46
<212> TYPE: PRT
<213> ORGANISM: Artificial
<220> FEATURE:
<223> OTHER INFORMATION: synthetic peptide

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala Cys
        35                  40                  45

<210> SEQ ID NO 6
<211> LENGTH: 46
<212> TYPE: PRT
<213> ORGANISM: Artificial
<220> FEATURE:
<223> OTHER INFORMATION: synthetic peptide

<400> SEQUENCE: 6

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala Cys
        35                  40                  45

<210> SEQ ID NO 7
<211> LENGTH: 16
<212> TYPE: PRT
<213> ORGANISM: Artificial
<220> FEATURE:
<223> OTHER INFORMATION: synthetic peptide

<400> SEQUENCE: 7

Gly Thr Ile Asn Val His Asp Val Glu Thr Gln Phe Asn Gln Tyr Cys
1               5                   10                  15

<210> SEQ ID NO 8
<211> LENGTH: 16
<212> TYPE: PRT
<213> ORGANISM: Artificial
<220> FEATURE:
<223> OTHER INFORMATION: synthetic peptide

<400> SEQUENCE: 8

Lys Thr Glu Ala Ala Ser Arg Tyr Asn Leu Thr Ile Ser Asp Val Cys
1               5                   10                  15

<210> SEQ ID NO 9
<211> LENGTH: 16
<212> TYPE: PRT
<213> ORGANISM: Artificial
<220> FEATURE:
<223> OTHER INFORMATION: synthetic peptide

<400> SEQUENCE: 9

Lys Thr Glu Ala Ala Ser Pro Tyr Asn Leu Thr Ile Ser Asp Val Cys
1               5                   10                  15

<210> SEQ ID NO 10
<211> LENGTH: 16
<212> TYPE: PRT
<213> ORGANISM: Artificial
<220> FEATURE:
<223> OTHER INFORMATION: synthetic peptide

<400> SEQUENCE: 10

Cys Ser Val Ser Asp Val Pro Phe Pro Phe Ser Ala Gln Ser Gly Ala
1               5                   10                  15

<210> SEQ ID NO 11
<211> LENGTH: 20
<212> TYPE: PRT
<213> ORGANISM: Artificial
<220> FEATURE:
<223> OTHER INFORMATION: synthetic peptide

<400> SEQUENCE: 11

Cys Arg Tyr Val Pro Pro Ser Ser Thr Asp Arg Ser Pro Tyr Glu Lys
1               5                   10                  15

Val Ser Ala Gly
            20

<210> SEQ ID NO 12
<211> LENGTH: 7
<212> TYPE: PRT
<213> ORGANISM: Artificial
<220> FEATURE:
<223> OTHER INFORMATION: synthetic peptide

<400> SEQUENCE: 12

Pro Asp Thr Arg Pro Ala Pro
1               5

<210> SEQ ID NO 13
<211> LENGTH: 7
<212> TYPE: PRT
<213> ORGANISM: Artificial
<220> FEATURE:
<223> OTHER INFORMATION: synthetic peptide

<400> SEQUENCE: 13

Thr Pro Ala Ser Lys Ser Thr
1               5

<210> SEQ ID NO 14
<211> LENGTH: 7
<212> TYPE: PRT
<213> ORGANISM: Artificial
<220> FEATURE:
<223> OTHER INFORMATION: synthetic peptide

<400> SEQUENCE: 14

Ser His His Ser Asp Thr Pro
1               5

<210> SEQ ID NO 15
<211> LENGTH: 7
<212> TYPE: PRT
<213> ORGANISM: Artificial
<220> FEATURE:
<223> OTHER INFORMATION: synthetic peptide

<400> SEQUENCE: 15

Thr Lys Thr Asp Ala Ser Ser

```
1               5

<210> SEQ ID NO 16
<211> LENGTH: 7
<212> TYPE: PRT
<213> ORGANISM: Artificial
<220> FEATURE:
<223> OTHER INFORMATION: synthetic peptide

<400> SEQUENCE: 16

Ser Ser Asn His Ser Thr Ser
1               5

<210> SEQ ID NO 17
<211> LENGTH: 7
<212> TYPE: PRT
<213> ORGANISM: Artificial
<220> FEATURE:
<223> OTHER INFORMATION: synthetic peptide

<400> SEQUENCE: 17

Glu Asp Pro Ser Thr Asp Tyr
1               5

<210> SEQ ID NO 18
<211> LENGTH: 7
<212> TYPE: PRT
<213> ORGANISM: Artificial
<220> FEATURE:
<223> OTHER INFORMATION: synthetic peptide

<400> SEQUENCE: 18

Phe Asn Gln Tyr Lys Thr Glu
1               5

<210> SEQ ID NO 19
<211> LENGTH: 7
<212> TYPE: PRT
<213> ORGANISM: Artificial
<220> FEATURE:
<223> OTHER INFORMATION: synthetic peptide

<400> SEQUENCE: 19

Cys Arg Arg Lys Asn Tyr Gly
1               5

<210> SEQ ID NO 20
<211> LENGTH: 7
<212> TYPE: PRT
<213> ORGANISM: Artificial
<220> FEATURE:
<223> OTHER INFORMATION: synthetic peptide

<400> SEQUENCE: 20

Tyr Pro Thr Tyr His Thr His
1               5

<210> SEQ ID NO 21
<211> LENGTH: 7
<212> TYPE: PRT
<213> ORGANISM: Artificial
<220> FEATURE:
<223> OTHER INFORMATION: synthetic peptide

<400> SEQUENCE: 21

Ser Thr Asp Arg Ser Pro Tyr
1               5
```

<210> SEQ ID NO 22
<211> LENGTH: 175
<212> TYPE: PRT
<213> ORGANISM: Homo Sapiens

<400> SEQUENCE: 22

Tyr Lys Gln Gly Gly Phe Leu Gly Leu Ser Asn Ile Lys Phe Arg Pro
1               5                   10                  15

Gly Ser Val Val Val Gln Leu Thr Leu Ala Phe Arg Glu Gly Thr Ile
            20                  25                  30

Asn Val His Asp Val Glu Thr Gln Phe Asn Gln Tyr Lys Thr Glu Ala
        35                  40                  45

Ala Ser Arg Tyr Asn Leu Thr Ile Ser Asp Val Ser Val Ser Asp Val
    50                  55                  60

Pro Phe Pro Phe Ser Ala Gln Ser Gly Ala Gly Val Pro Gly Trp Gly
65                  70                  75                  80

Ile Ala Leu Leu Val Leu Val Cys Val Leu Val Ala Leu Ala Ile Val
                85                  90                  95

Tyr Leu Ile Ala Leu Ala Val Cys Gln Cys Arg Arg Lys Asn Tyr Gly
            100                 105                 110

Gln Leu Asp Ile Phe Pro Ala Arg Asp Thr Tyr His Pro Met Ser Glu
        115                 120                 125

Tyr Pro Thr Tyr His Thr His Gly Arg Tyr Val Pro Pro Ser Ser Thr
    130                 135                 140

Asp Arg Ser Pro Tyr Glu Lys Val Ser Ala Gly Asn Gly Gly Ser Ser
145                 150                 155                 160

Leu Ser Tyr Thr Asn Pro Ala Val Ala Ala Thr Ser Ala Asn Leu
                165                 170                 175

<210> SEQ ID NO 23
<211> LENGTH: 175
<212> TYPE: PRT
<213> ORGANISM: Homo Sapiens

<400> SEQUENCE: 23

Tyr Lys Gln Gly Gly Phe Leu Gly Leu Ser Asn Ile Lys Phe Arg Pro
1               5                   10                  15

Gly Ser Val Val Val Gln Leu Thr Leu Ala Phe Arg Glu Gly Thr Ile
            20                  25                  30

Asn Val His Asp Val Glu Thr Gln Phe Asn Gln Tyr Lys Thr Glu Ala
        35                  40                  45

Ala Ser Arg Tyr Asn Leu Thr Ile Ser Asp Val Ser Val Ser Asp Val
    50                  55                  60

Pro Phe Pro Phe Ser Ala Gln Ser Gly Ala Gly Val Pro Gly Trp Gly
65                  70                  75                  80

Ile Ala Leu Leu Val Leu Val Cys Val Leu Val Ala Leu Ala Ile Val
                85                  90                  95

Tyr Leu Ile Ala Leu Ala Val Cys Gln Cys Arg Arg Lys Asn Tyr Gly
            100                 105                 110

Gln Leu Asp Ile Phe Pro Ala Arg Asp Thr Tyr His Pro Met Ser Glu
        115                 120                 125

Tyr Pro Thr Tyr His Thr His Gly Arg Tyr Val Pro Pro Ser Ser Thr
    130                 135                 140

Asp Arg Ser Pro Tyr Glu Lys Val Ser Ala Gly Asn Gly Gly Ser Ser
145                 150                 155                 160

-continued

Leu Ser Tyr Thr Asn Pro Ala Val Ala Ala Thr Ser Ala Asn Leu
            165                 170                 175

<210> SEQ ID NO 24
<211> LENGTH: 74
<212> TYPE: PRT
<213> ORGANISM: Homo Sapiens

<400> SEQUENCE: 24

Ala Val Cys Gln Cys Arg Arg Lys Asn Tyr Gly Gln Leu Asp Ile Phe
1               5                   10                  15

Pro Ala Arg Asp Thr Tyr His Pro Met Ser Glu Tyr Pro Thr Tyr His
            20                  25                  30

Thr His Gly Arg Tyr Val Pro Pro Ser Ser Thr Asp Arg Ser Pro Tyr
        35                  40                  45

Glu Lys Val Ser Ala Gly Asn Gly Gly Ser Ser Leu Ser Tyr Thr Asn
    50                  55                  60

Pro Ala Val Ala Ala Thr Ser Ala Asn Leu
65                  70

<210> SEQ ID NO 25
<211> LENGTH: 175
<212> TYPE: PRT
<213> ORGANISM: Homo Sapiens

<400> SEQUENCE: 25

Tyr Lys Gln Gly Gly Phe Leu Gly Leu Ser Asn Ile Lys Phe Arg Pro
1               5                   10                  15

Gly Ser Val Val Val Gln Leu Thr Leu Ala Phe Arg Glu Gly Thr Ile
            20                  25                  30

Asn Val His Asp Val Glu Thr Gln Phe Asn Gln Tyr Lys Thr Glu Ala
        35                  40                  45

Ala Ser Arg Tyr Asn Leu Thr Ile Ser Asp Val Ser Val Ser Asp Val
    50                  55                  60

Pro Phe Pro Phe Ser Ala Gln Ser Gly Ala Gly Val Pro Gly Trp Gly
65                  70                  75                  80

Ile Ala Leu Leu Val Leu Val Cys Val Leu Val Ala Leu Ala Ile Val
                85                  90                  95

Tyr Leu Ile Ala Leu Ala Val Cys Gln Cys Arg Arg Lys Asn Tyr Gly
            100                 105                 110

Gln Leu Asp Ile Phe Pro Ala Arg Asp Thr Tyr His Pro Met Ser Glu
        115                 120                 125

Tyr Pro Thr Tyr His Thr His Gly Arg Tyr Val Pro Pro Ser Ser Thr
    130                 135                 140

Asp Arg Ser Pro Tyr Glu Lys Val Ser Ala Gly Asn Gly Gly Ser Ser
145                 150                 155                 160

Leu Ser Tyr Thr Asn Pro Ala Val Ala Ala Thr Ser Ala Asn Leu
                165                 170                 175

<210> SEQ ID NO 26
<211> LENGTH: 129
<212> TYPE: PRT
<213> ORGANISM: Homo Sapiens

<400> SEQUENCE: 26

Ile Asn Lys Gly Val Phe Trp Ala Ser Pro Ile Leu Ser Ser Val Ser
1               5                   10                  15

```
Asp Val Pro Phe Pro Phe Ser Ala Gln Ser Gly Ala Gly Val Pro Gly
            20                  25                  30

Trp Gly Ile Ala Leu Leu Val Leu Val Cys Val Leu Val Ala Leu Ala
        35                  40                  45

Ile Val Tyr Leu Ile Ala Leu Ala Val Cys Gln Cys Arg Arg Lys Asn
50                  55                  60

Tyr Gly Gln Leu Asp Ile Phe Pro Ala Arg Asp Thr Tyr His Pro Met
65                  70                  75                  80

Ser Glu Tyr Pro Thr Tyr His Thr His Gly Arg Tyr Val Pro Pro Ser
            85                  90                  95

Ser Thr Asp Arg Ser Pro Tyr Glu Lys Val Ser Ala Gly Asn Gly Gly
            100                 105                 110

Ser Ser Leu Ser Tyr Thr Asn Pro Ala Val Ala Ala Thr Ser Ala Asn
            115                 120                 125

Leu

<210> SEQ ID NO 27
<211> LENGTH: 173
<212> TYPE: PRT
<213> ORGANISM: Mus Musculus

<400> SEQUENCE: 27

Phe Asn Gly Asp Phe Leu Gly Ile Ser Ser Ile Lys Phe Arg Ser Gly
1               5                   10                  15

Ser Val Val Val Glu Ser Thr Val Val Phe Arg Glu Gly Thr Phe Ser
            20                  25                  30

Ala Ser Asp Val Lys Ser Gln Leu Ile Gln His Lys Lys Glu Ala Asp
        35                  40                  45

Asp Tyr Asn Leu Thr Ile Ser Glu Val Lys Val Asn Glu Met Gln Phe
    50                  55                  60

Pro Pro Ser Ala Gln Ser Arg Pro Gly Val Pro Gly Trp Gly Ile Ala
65                  70                  75                  80

Leu Leu Val Leu Val Cys Ile Leu Val Ala Leu Ala Ile Val Tyr Phe
                85                  90                  95

Leu Ala Leu Ala Val Cys Gln Cys Arg Arg Lys Ser Tyr Gly Gln Leu
            100                 105                 110

Asp Ile Phe Pro Thr Gln Asp Thr Tyr His Pro Met Ser Glu Tyr Pro
        115                 120                 125

Thr Tyr His Thr His Gly Arg Tyr Val Pro Pro Gly Ser Thr Lys Arg
    130                 135                 140

Ser Pro Tyr Glu Glu Val Ser Ala Gly Asn Gly Ser Ser Ser Leu Ser
145                 150                 155                 160

Tyr Thr Asn Pro Ala Val Val Thr Ser Ala Asn Leu
                165                 170

<210> SEQ ID NO 28
<211> LENGTH: 173
<212> TYPE: PRT
<213> ORGANISM: Rattus Norvegicus

<400> SEQUENCE: 28

Phe Asn Gly Asp Phe Leu Gly Val Ser Thr Ile Lys Phe Arg Ser Gly
1               5                   10                  15

Ser Val Val Val Ala Ser Thr Val Ile Phe Arg Glu Gly Thr Phe Ser
            20                  25                  30

Ala Ser Glu Val Lys Ser Gln Leu Val Gln His Lys Lys Glu Ala Ala
```

-continued

```
             35                   40                  45
Asp Tyr Asn Leu Thr Ile Ser Glu Val Asn Val Asn Glu Met Gln Phe
        50                  55              60

Pro Ser Ser Ala Gln Ser Trp Pro Gly Val Pro Gly Trp Gly Ile Ala
65                      70              75                  80

Leu Leu Val Leu Val Cys Ile Leu Val Ala Leu Val Ile Val Tyr Leu
                85                  90              95

Ile Ala Leu Ala Leu Cys Gln Cys Arg Arg Lys Ser Tyr Gly Gln Leu
                100             105             110

Asp Leu Phe Pro Thr Arg Asp Thr Tyr His Pro Met Ser Glu Tyr Pro
            115             120             125

Thr Tyr His Thr His Gly Arg Tyr Val Pro Pro Ala Thr Thr Lys Arg
        130             135             140

Ser Pro Tyr Glu Glu Val Ser Thr Gly Asn Gly Ser Ser Gly Leu Ser
145                 150             155             160

Tyr Thr Asn Pro Ala Val Ala Thr Thr Ser Ala Asn Leu
                165             170
```

ANTIBODY AGAINST MUCIN 1 (MUC1) PROTEIN AND USE OF SAME

CROSS-REFERENCE TO RELATED APPLICATIONS

This application is a 371 of PCT/JP2011/052893, filed Feb. 10, 2011, which claims the benefit of Japanese Patent Application Nos. 2010-028729, filed Feb. 12, 2010and 2010-097922, filed Apr. 21, 2010, the contents of each of which are incorporated herein by reference.

BACKGROUND OF THE INVENTION

1. Field of the Invention

The present invention relates to a novel anti-mucin 1 protein antibody and a reagent for immunoassay containing the same. The present invention also relates to a reagent and a method for determining a disease or disorder associated with human mucin 1 protein.

2. Background Art

Gastric cancer is a frequent cancer, ranking first for males and second for females in the frequency of Japanese morbidity of malignant tumors; internationally, many patients with gastric cancer are present in Asia such as China, Japan, and Korea and South America. Even in these days of advanced diagnostic imaging and endoscopy, the number of deaths from gastric cancer was 49,535 (32,142 for males and 17,393 for females) in Japan in 2003, and gastric cancer was second only to lung cancer for males and second only to colon cancer for females in that number (from the Population Survey Report conducted by the Health the Labour and Welfare Ministry, Japan).

Among various tissue types of gastric cancer, "poorly differentiated adenocarcinoma: non-solid type" (abbr. "por2") and "signet-ring cell carcinoma" (abbr. "sig") are of particularly high malignancy and also often have the state of "scirrhous gastric cancer," many cases of which have already been in the situation of "being too late" when detected and which corresponds to "type 4" for the macroscopic tumor.

"Scirrhous gastric cancer" is the most malignant cancer among gastric cancers and occurs in the mucosa like other gastric cancers; however, it has the characteristic of widely spreading in the stomach wall while not causing prominent change in the mucosal surface. "Scirrhous gastric cancer" accounts for about 10% of all gastric cancers, is often found in the young generations in their thirties and forties, and is hard to be diagnosed even by specialists; about 60% of such patients have already had peritoneal metastasis or broad lymph node metastasis at the time of detection, and it is often the case that cancer has already progressed when recognized by complaints of anxiety about the physical condition. Even if the cancer can be removed by surgery, it has high recurrence rate. The metastasis typical of "scirrhous gastric cancer" is peritoneal dissemination, which occurs in about one-half of individuals affected by cancer of this type.

The final definite diagnosis of gastric cancer is performed by the histopathological diagnosis of a biopsy specimen under endoscopy; however, the common hematoxylin-eosin (HE) staining of gastric biopsy tissue is at a high risk of "detection failure of cancer" because cancer cells are often among proliferated granulation tissue and fibrous tissue and difficult to determine where the cancer cells are. To prevent detection failure of cancer, some pathological test facilities perform periodic acid-Schiff stain (PAS stain) as a specific stain in all gastric biopsy specimens. However, the PAS stain also often fails to identify gastric cancer cells because it also stains non-cancer substances such as inflammatory cells frequently present around the gastric cancer cells. "Detection failure of cancer" must be avoided by all means particularly in a gastric biopsy specimen of a case suspected of "scirrhous gastric cancer" which is clinically difficult to diagnose.

As described above, the accurate histopathological diagnosis of "poorly differentiated adenocarcinoma: non-solid type (por2)" or "signet-ring cell carcinoma (sig)" having a strong tendency to become "scirrhous gastric cancer" is extremely effective in the early detection of "scirrhous gastric cancer" and essential for improving the outcome of gastric cancer treatment. For the histopathological diagnosis, the need for immunostaining based on a protein or sugar chain specifically expressed in pathological tissue of gastric cancer becomes increasingly important, and the development competition of an antibody therefore is being intensified.

Mucin-type glycoproteins are mucous substances contained in the mucus for protecting the mucosa of the intestinal tract, respiratory tract, oral cavity, uterus, etc. in the animals, and are proteins having many sugar chains (called mucin-type sugar chains). For human, 18 types are reported as those of mucin (MUC) genes encoding such proteins; 11 types thereof encode transmembrane-type proteins and 7 types encode secretory-type proteins. The mucin genes are reported to be associated with various diseases, for example, cancer, inflammatory bowel disease, asthma, and the like. For example, the expression of mucin 1 (MUC1) has been shown to be associated with the poor prognosis of patients with various human cancers (pancreatic cancer, bile duct cancer, gastric cancer, esophageal cancer, breast cancer, lung cancer, and the like) (Yonezawa S, Goto M. Yamada N, Higashi M, Nomoto M: Expression profiles of MUC1, MUC2 and MUC4 mucins in human neoplasms and their relationship with biological behavior. Proteomics 8 (16): 3329-3341, 2008).

MUC1 was earliest cloned among mucin antigens considered dominant as tumor markers, and the number of antibodies against MUC1 is now more than 400. For example, there are reported an antibody recognizing and reacting with a sugar chain present in the tandem repeat of the extracellular region of the MUC1 protein and an antibody recognizing and reacting with amino acids 1,110 to 1,155 (45 amino acids) corresponding to the C-terminal side of the cleavage sate at the extracellular region thereof (Mahanta S, et al.: PLoS ONE vol 3. Issue 4. e2054, 2008). However, as described above, there has remained a need for the development of an antibody capable of sensitively and simply detecting cancer cells of poorly differentiated adenocarcinoma or signet-ring cell carcinoma which has particularly high malignancy among gastric cancers, is difficult to find out by diagnostic imaging or endoscopy, and is at a high risk of detection failure by usual hematoxylin-eosin (HE) staining even in the pathological diagnosis of gastric biopsy tissue providing the final diagnosis.

SUMMARY OF INVENTION

Accordingly, an object of the present invention is to provide means and a method enabling clear staining of cancer cells of poorly differentiated adenocarcinoma or signet-ring cell carcinoma and assuring the effectiveness of early diagnosis of human cancers including these gastric cancers easily becoming too late.

As a result of intensive studies for solving the above problems, the present inventor has found that when an antibody is prepared using a particular region of human mucin 1 protein (MUC1) as an antigen, the resulting anti-MUC1 antibody specifically reacts with the MUC1 protein expressed on gastric cancer cells, resulting in enabling the clear immunostaining of these cancer cells (particularly, poorly differentiated adenocarcinoma and signet-ring cell carcinoma). Cancer cells such as colon cancer and pancreatic cancer and samples such as a metastatic focus sample and an ascites cytodiagnosis sample have been capable of being immunostained using the anti-MUC1 antibody. Because MUC1 has been confirmed to be expressed in various diseases and disorders, the present inventor has obtained the finding that the use of the above anti-MUC1 antibody can determine diseases or disorders associated with MUC1.

Thus, the present invention relates to the following (1) to (14).

(1) An antibody wherein the antibody is prepared using a peptide of (a) or (b) below as an antigen and is reactive with human mucin 1 (MUC1) protein:
- (a) a peptide comprising at least contiguous amino acids at positions 69 to 75 (amino acids at positions 1,223 to 1,229 of the full-length MUC1 of SEQ ID NO: 3) in the amino acid sequence of SEQ ID NO: 2; or
- (b) a peptide consisting of an amino acid sequence in which one or several amino acids are deleted, substituted or added in at least contiguous amino acids at positions 69 to 75 (amino acids at positions 1,223 to 1,229 of the full-length MUC1 of SEQ ID NO: 3) in the amino acid sequence of SEQ ID NO: 2, and having the antigenicity of human MUC1 protein.

(2) The antibody according to (1), wherein at least contiguous amino acids at positions 69 to 75 in the amino acid sequence of SEQ ID NO: 2 is at least contiguous amino acids at positions 63 to 81 in the amino acid sequence of SEQ ID NO: 2.

(3) The antibody according to (1) or (2), wherein the peptide consists of the amino acid sequence of SEQ ID NO: 1.

(4) The antibody according to any of (1) to (3), wherein the antibody is a monoclonal antibody or a polyclonal antibody.

(5) The antibody according to any of (1) to (4), wherein the antibody is labeled.

(6) An immunoassay reagent for human mucin 1 (MUC1) protein, comprising the antibody according to any of (1) to (5).

(7) A reagent for determining a disease or disorder associated with human mucin 1 (MUC1) protein, comprising the antibody according to any of (1) to (5).

(8) The reagent according to (7), wherein the disease or disorder associated with human mucin 1 (MUC1) protein is selected from the group consisting of gastric cancer, pancreatic cancer, bile duct cancer, colon cancer, ovarian cancer, breast cancer, and lung cancer.

(9) The reagent according to (8), wherein the gastric cancer is poorly differentiated adenocarcinoma or signet-ring cell carcinoma.

(10) A method for determining a disease or disorder associated with human mucin 1 (MUC1) protein in a subject, comprising the steps of:
- (a) contacting the antibody according to any of (1) to (5) with a sample from the subject; and
- (b) detecting whether the antibody has bound to human mucin 1 (MUC1) protein in the sample or not.

(11) The method according to (10), wherein the disease or disorder associated with human mucin 1 (MUC1) protein is selected from the group consisting of gastric cancer, pancreatic cancer, bile duct cancer, colon cancer, ovarian cancer, breast cancer, and lung cancer.

(12) The method according to (11), wherein the gastric cancer is poorly differentiated adenocarcinoma or signet-ring cell carcinoma.

(13) The method according to any of (10) to (12), wherein the sample is selected from the group consisting of a biopsy tissue sample, a surgically resected tissue sample, and a cytodiagnostic sample.

(14) A peptide of (a) or (b) below:
- (a) a peptide comprising at least contiguous amino acids at positions 69 to 75 (amino acids at positions 1,223 to 1,229 of the full-length MUC1 of SEQ ID NO: 3) in the amino acid sequence of SEQ ID NO: 2; or
- (b) a peptide consisting of an amino acid sequence in which one to several amino acids are deleted, substituted or added in at least contiguous amino acids at positions 69 to 75 (amino acids at positions 1,223 to 1,229 of the full-length MUC1 of SEQ ID NO: 3) in the amino acid sequence of SEQ ID NO: 2, and having the antigenicity of human MUC1 protein.

According to the present invention, there are provided an antibody against human mucin 1 (MUC1) protein and an antigen peptide for preparing the antibody. The use of the anti-MUC1 antibody of the present invention can sensitively, reliably, and simply detect the presence of MUC1 protein, resulting in enabling the determination of a disease or disorder associated with MUC1. Particularly, the anti-MUC1 antibody of the present invention can stain gastric cancer cells of poorly differentiated adenocarcinoma: non-solid type (por2) and signet-ring cell carcinoma (sig) at an extremely high rate and clearly and may be useful in the medical diagnosis field and the pharmaceutical field.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2 shows the positions of epitopes, a cleavage site, and a transmembrane region in the amino acid sequence (amino acids 901-1,255) of human MUC1 protein (SEQ ID NO: 3).

In FIG. 5, CS represents a cleavage site, and TM represents a transmembrane region.

FIG. 12 is a series of photographs showing the results of immunostaining of (A) the poorly differentiated adenocarcinoma: non-solid type (por2) of the stomach and (B) the lymph node metastatic focus of the poorly differentiated adenocarcinoma of the colon using the anti-MUC1 antibody of the present invention together with results by other immunostaining methods.

FIG. 15 is a series of photographs showing a result of immunostaining of normal pancreatic tissue using the anti-MUC1 antibody of the present invention.

DETAILED DESCRIPTION OF THE INVENTION

The present invention will be described in detail below. This application claims priority to Japanese Patent Application No. 2010-028729, filed on Feb. 12, 2010 and Japanese Patent Application No. 2010-097922, filed on Apr. 21, 2010, claiming priority to the Japanese Patent Application, and encompasses the contents of the specifications and/or drawings of the above patent applications.
1. Antigen Peptide and Antibody The present invention provides a novel antibody against human mucin 1 (MUC1) protein. Mucin proteins are mucous substances contained in the mucus, and are proteins having many sugar chains (called mucin-type sugar chains). Mucin 1 (MUC1) as one of the mucin proteins is expressed in the luminal structures of the respiratory apparatus, genital organ, and gastrointestine (Mahanta S, et al.: PLoS ONE vol 3. Issue 4. e2054, 2008) and has been isolated from humans, mice, rats, and others; the sequences thereof have also been elucidated. For example, the gene of human (Homo sapiens) mucin 1 is deposited under the accession number 4582 or J05582.1, and the protein thereof is deposited under the accession number AAA60019.1 and the sequences of precursors of their isotypes 1 to 6 are deposited under the accession numbers NP_002447.4, NP_001018016.1, NP_001018017.1, NP_001037855.1, and NP_001037856.1. The amino acid sequence and nucleotide sequence of human mucin 1 are shown in SEQ ID NOS: 3 and 4, respectively. Known mucin 1 derived from other animals include mouse (Mus musculus) mucin 1 (gene: accession number 17829, protein: accession number NP_038633.1), and rat (Rattus norvegicus) mucin 1 (gene: accession number 24571, protein: accession number NP_036734.1).

Figure 1:
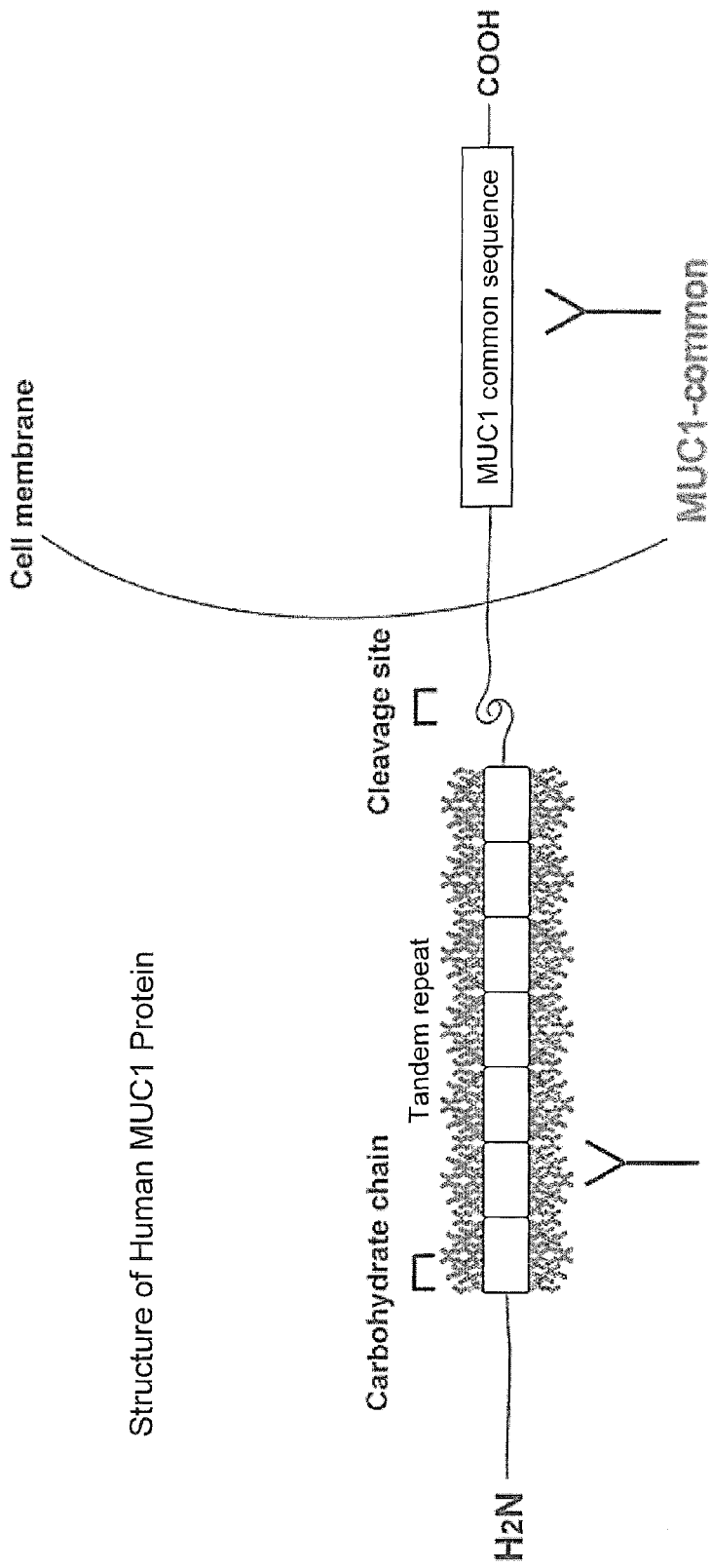
FIG. 1 is a diagram showing the structure of human mucin 1 (MUC1) protein and a target site by an anti-MUC1 antibody.

The antibody according to the present invention is generated against a portion of a human MUC1 molecule at the cytoplasmic tail interior to the cell membrane as an antigen (shown as "MUC1-common" in FIG. 1). In contrast, the conventional anti-MUC1 antibodies have been generated against a core peptide portion consisting of repeated sequences called "tandem repeats" present in the upper part of the structure projecting long toward the outside of a cell, of an MUC1 molecule (one example thereof is shown as "MUC1-DF3" in FIG. 1). The present inventor has also succeeded in preparing an anti-MUC1 antibody capable of reacting with human MUC1 protein and clearly immunostaining tumor cells, especially gastric cancer cells and an ascites cytodiagnosis sample including poorly differentiated adenocarcinoma: non-solid type (por2), colon cancer cells including poorly differentiated adenocarcinoma and a metastatic focus sample thereof, and pancreatic tumor cells including pancreatic cancer and a pancreatic juice thereof or a tissue of pancreaticobiliary duct cystic tumor by using a region different from that for the conventional antigen design as an antigen.

Figure 3:
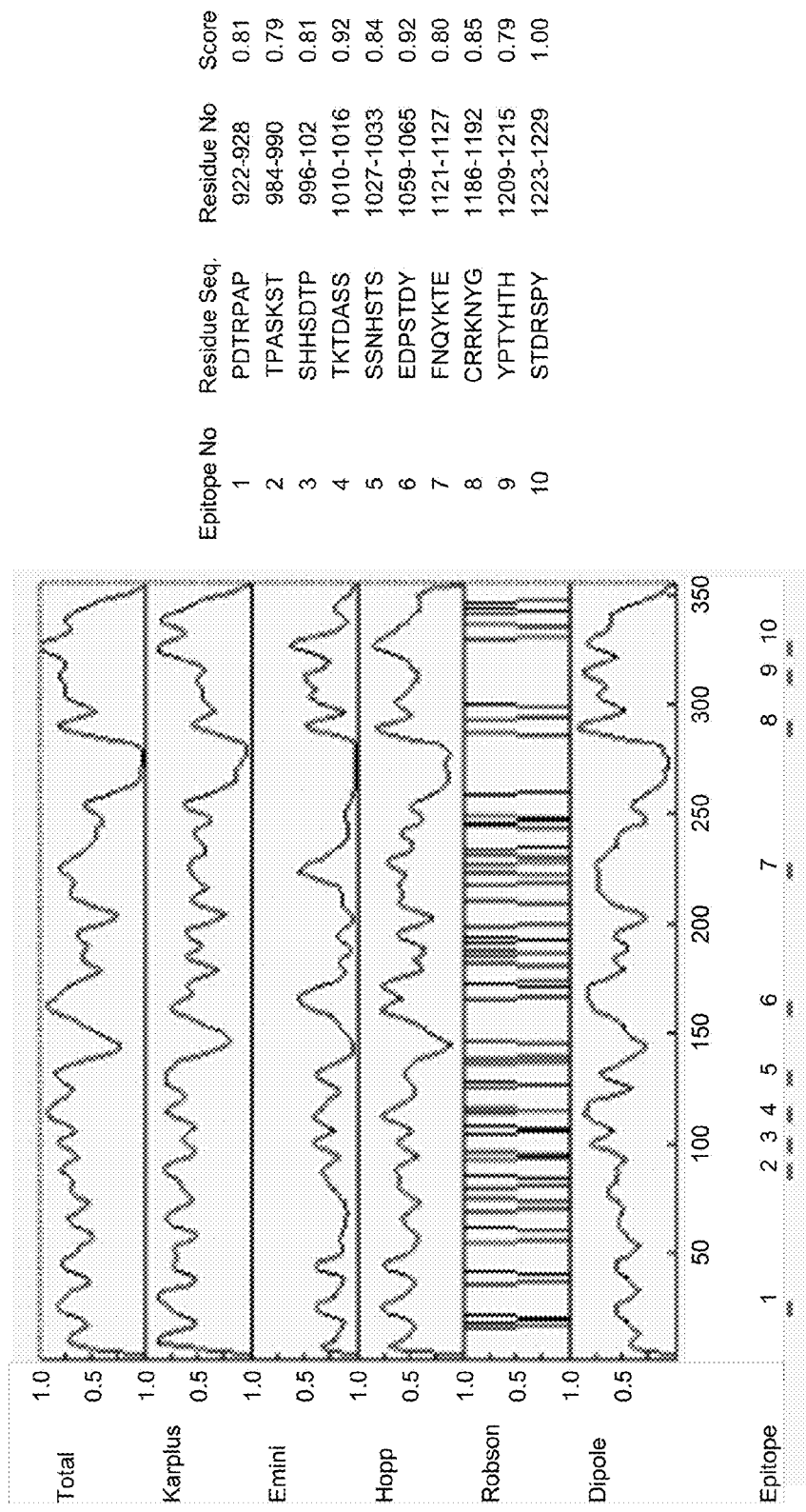
FIG. 3 shows the results of epitope prediction in human MUC1 protein. The amino acid sequences of Epitope Nos. 1-10 correspond to SEQ ID NOs. 12-21, respectively.
Figure 4:
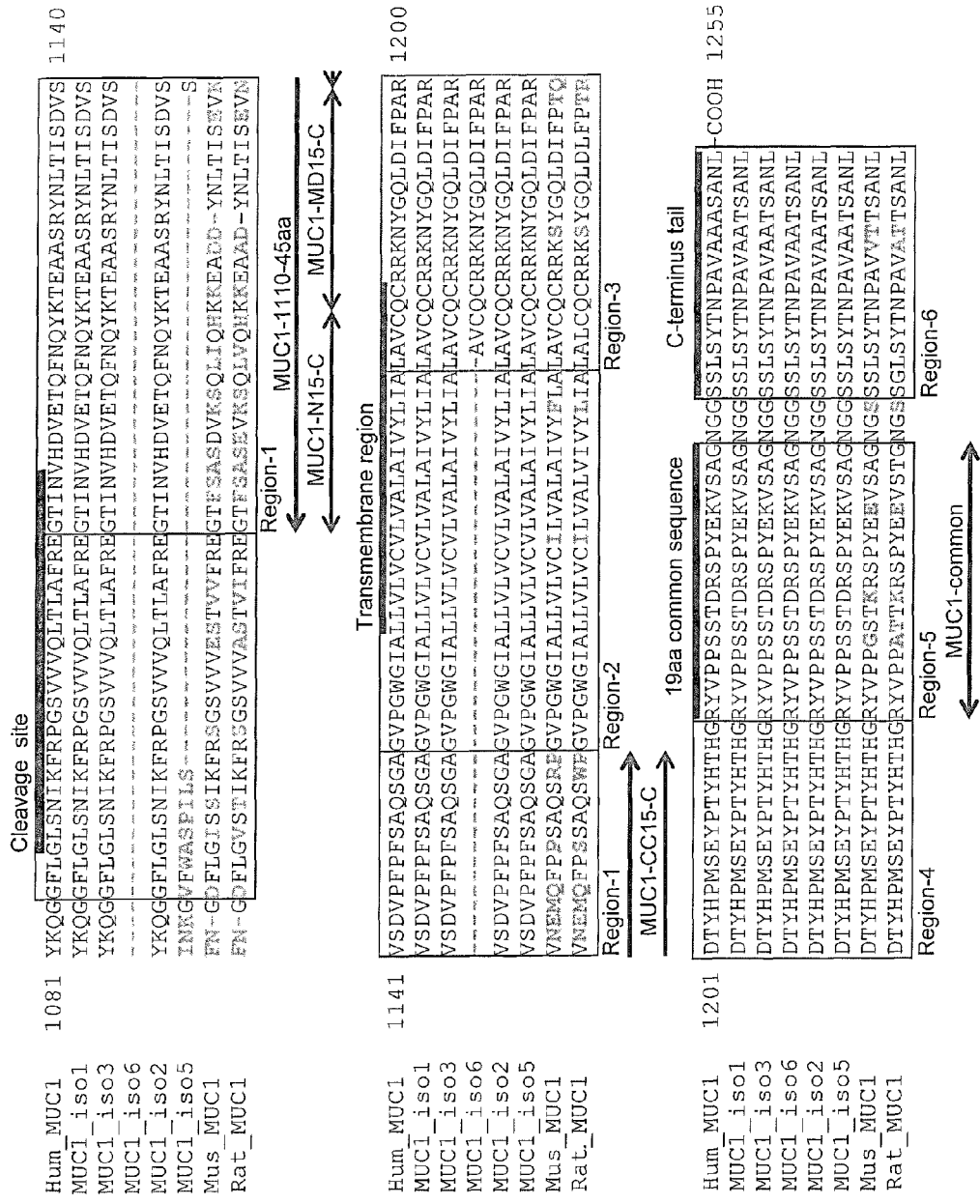
FIG. 4 shows a comparison of the amino acid sequence of human MUC1 protein (SEQ ID NO: 3), corresponding to residues 1081-1255 of SEQ ID NO:3, with human isotypes of MUC1 (MUC1 iso1: SEQ ID NO. 22, MUC1 iso3: SEQ ID NO. 23, MUC1 iso6: SEQ ID NO. 24, MUC1 iso2: SEQ ID NO. 25, and MUC1 iso5: SEQ ID NO. 26) and mouse and rat homologs (Mus MUC1: SEQ ID NO: 27, and Rat MUC1: SEQ ID NO: 28).

As shown in FIG. 4, the sequence of Region-5 (SEQ ID NO: 1) selected as an antigen is based on the portion highly conserved in human MUC1 protein and its isotypes (isotypes 1, 2, 3, 5, and 6), that is, the sequence of 84 amino acids comprising Region-2 to Region-5 (SEQ ID NO: 2). Therefore, the antigenicity of these regions may not be affected by an individual difference, but Region-4 alone, which has proved to be not different between humans and mice by homology analysis, does not serve as an immunogen as a heterologous protein and Region-2 alone, which has proved to have no antigen determinant by a predictive analysis of B-cell epitopes, also less easily serves as an immunogen; thus, the range of antigen candidates was narrowed to the two regions of Region-3 and Region-5 containing Epitope No. 8 (SEQ ID NO: 19) and Epitope No. 10 (SEQ ID NO: 21), respectively, which have proved to be antigen determinants by predictive analysis of B-cell epitopes. Finally, Epitope No. 10 (STDRSPY; SEQ ID NO: 21) (FIG. 3) getting a high score in epitope analysis has been selected, and as an immunogen, there has been used a peptide comprising the region of Region-5 of 19 amino acids (RYVPPSSTDRSPYEKVSAG: SEQ ID NO: 1) containing the epitope. Epitope No. 10 corresponds to the amino acids at positions 7-13 of SEQ ID NO: 1 (Region-5), the amino acids at positions 69-75 of SEQ ID NO: 2 (Region-2 to Region-5), and amino acids at positions 1,223-1,229 of SEQ ID NO: 3 (full-length mucin 1).

In the present invention, the peptide used as an antigen to generate the antibody according to the present invention is referred to as "antigen peptide." The invention relates to an antigen peptide, specifically a peptide designed on the basis of 84 amino acids at positions 1,155 to 1,238 (SEQ ID NO: 2) in human MUC1 protein of SEQ Ill NO: 3 (full-length human MUC1). More specifically, a peptide containing at least contiguous amino acids at positions 69 to 75 (amino acids at positions 1,223 to 1,229 of the full-length MUC1 of SEQ ID NO: 3) in the amino acid sequence of SEQ ID NO: 2) nay be used as the antigen peptide. Preferably, as the antigen peptide, a peptide containing at least contiguous amino acids at positions 63 to 81 (amino acids at positions 1,217 to 1,235 of the full-length MUC1) in the amino acid sequence of SEQ ID NO: 2, particularly preferably a peptide consisting of contiguous amino acids at positions 63 to 81 (amino acids at positions 1,217 to 1,235 of the full-length MUC1) (SEQ ID NO: 1) is used. When an antibody is prepared using such an antigen peptide as an antigen, the resultant antibody can react with the full-length human MUC1 protein as well as the antigen peptide.

For the purpose of the present invention, the antigen peptide may be a peptide consisting of an amino acid sequence in which one to several amino acids are deleted, substituted or added in at least contiguous amino acids at positions 69 to 75 (amino acids at positions 1,223 to 1,229 of the full-length MUC1) in the amino acid sequence of SEQ ID NO: 2 or preferably the amino acid sequence of SEQ ID NO: 1 provided that it maintains the antigenicity of human MUC1 protein. For example, 1 to 3, preferably 1 to 2 amino acids may be deleted in at least contiguous amino acids at positions 69 to 75 (amino acids at positions 1,223 to 1,229 of the full-length MUC1) in the amino acid sequence of SEQ ID NO: 2 or preferably the amino acid sequence of SEQ ID NO: 1; 1 to 3, preferably 1 to 2 amino acids may be added in at least contiguous amino acids at positions 69 to 75 (amino acids at positions 1,223 to 1,229 of the full-length MUC1) in the amino acid sequence of SEQ ID NO: 2 or preferably the amino acid sequence of SEQ ID NO: 1; or 1 to 3, preferably 1 to 2 amino acids may be substituted by other amino acids in at least contiguous amino acids at positions 69 to 75 (amino acids at positions 1,223 to 1,229 of the full-length MUC1) in the amino acid sequence of SEQ ID NO: 2 or preferably the amino acid sequence of SEQ ID NO: 1. Particularly preferably, 1 to several amino acids may be substituted by conservative substitutions in at least contiguous amino acids at positions 69 to 75 (amino acids at positions 1,223 to 1,229 of the full-length MUC1) in the amino acid sequence of SEQ ID NO: 2 or preferably the amino acid sequence of SEQ ID NO: 1. The "conservative substitution" refers to the substitution of an amino acid by an amino acid exhibiting properties similar to those of the amino acid, which is known in the art. For example, a neutral (polar) amino acid (Asn, Ser, Gln, Thr, Tyr, or Cys), a neutral (non-polar, i.e., hydrophobic) amino acid (Gly, Trp, Met, Pro, Phe, Ala, Val, Leu, or Ile), an acidic (polar) amino acid (Asp or Glu), or a basic (polar) amino acid (Arg, His, or Lys) can be substituted by an amino acid having the same properties.

For example, in the present invention, there may also be used a peptide consisting of an amino acid sequence having at least 90% or more, preferably 95% or more homology or identity to at least contiguous amino acids at positions 69 to 75 (amino acids at positions 1,223 to 1,229 of the full-length MUC1) in the amino acid sequence of SEQ ID NO: 2 or preferably the amino acid sequence of SEQ ID NO: 1. The homology or identity between amino acid sequences can be easily determined by a method known in the art.

The antigenicity of human MUC1 protein means the ability thereof to produce an anti-MUC 1 antibody as an antigen. Whether a peptide has the antigenicity of human MUC1 protein or not can be confirmed by preparing an antibody against the peptide and detecting whether the prepared antibody reacts with the full-length human MUC1 protein or a protein derived therefrom (for example, the protein after being cut at the cleavage site) or not. Such procedures are known in the art.

The antigen peptide may be chemically synthesized on the basis of a designed amino acid sequence, or may be produced by transforming a host with a nucleic acid encoding it and recovering the peptide expressed in the host.

In the case of the chemical synthesis, the antigen peptide can be synthesized according to a known peptide synthesis technique, for example, using a commercial peptide synthesizer or a commercial kit for peptide synthesis. A technique for peptide synthesis is described, for example, in Peptide Synthesis, Interscience, New York, 1996; The Proteins, Vol. 2, Academic Press Inc., New York, 1976; Peptide Synthesis, Maruzen Company Ltd., 1975; Basis and Experiment of Peptide Synthesis, Maruzen Company Ltd., 1985; and other references, and International Publication WO99/67288 and other patent publications.

The peptide synthesis method may be a solid phase method or a liquid phase method provided that a desired antigen peptide sequence can be obtained. For example, the antigen peptide may be synthesized by a solid phase method using an Fmoc (9-fluorenylmethoxycarbonyl)/PyBOP (benzoyltriazol-1-yl-oxy-tris-pyrrolidino-phosphonium-hexafluorophosphate) process.

When a genetic recombination technique is used, a nucleic acid encoding the antigen peptide can be obtained by a reverse transcriptase-polymerase chain reaction (RT-PCR) using primers designed based on the sequence of the gene encoding human MUC1 protein by use of mRNA purified from RNA extracted from a tissue or cells of the stomach or the like, a gastric mucus, or the like as a template, or screening of a cDNA library using a probe designed based on the sequence of the gene encoding human MUC I protein. Alternatively, a nucleic acid encoding the antigen peptide can be obtained by performing a nucleic acid amplification reaction (e.g., PCR) using primers designed based on the sequence of the gene encoding human MUC1 protein by using DNA extracted from a tissue or cells of the stomach or the like, a gastric mucus, or the like as a template. A method for preparing a nucleic acid encoding an antigen peptide containing mutation(s) may be a method known in the art, for example, a site-directed mutagenesis method.

According to the present invention, an expression vector for recombinantly expressing the antigen peptide can be obtained by linking the above nucleic acid to an appropriate vector. The above nucleic acid or expression vector can be introduced into host cells such that the desired antigen peptide can be expressed to prepare a transformant. The preparation of such a transformant is well-known in the art, and can be performed by appropriately selecting the vector, host cells, and others used, by those of ordinary skill in the art. The antigen peptide of human MUC1 protein can be obtained by culturing the transformant into which the nucleic acid encoding the antigen peptide is introduced, followed by collection from the culture. The "culture" means any of a culture supernatant, cultured cells, and disrupted cells. Culturing the transformant in a medium can be carried out according to a conventional method used for the culture of a host. After culture, when the antigen peptide is produced within cells or microorganisms, the peptide is extracted by disrupting the cells or the microorganisms. When the antigen peptide is produced outside cells or microorganisms, the culture solution may be directly used or subjected to the removal of the cells or the microorganisms by centrifugation or the like.

The antigen peptide produced by the chemical synthesis or the recombination technique can be isolated and purified using general biochemical methods used for the isolation and purification of protein, such as ammonium sulfate precipitation, gel chromatography, ion exchange chromatography, or affinity chromatography, alone or in an appropriate combination thereof.

Whether a desired antigen peptide has been obtained or not can be confirmed by polyacrylamide gel electrophoresis, sodium dodecyl sulfate-polyacrylamide gel electrophoresis (SDS-PAGE), or the like.

The antigen peptide prepared as described above can be used to prepare an antibody against human MUC1 protein. In that case, a carrier protein may be bound to enhance its antigenicity. For example, a carrier protein may be bound such as keyhole limpet hemocyanin (KLH), bovine serum albumin (BSA), or ovalbumin (OVA). These carrier proteins are known in the art, and kits are also commercially available. Thus, such a known method or kit can be used to allow one or a plurality of carrier proteins to bind to the antigen peptide. The antigen peptide prepared above can also be used to purify an antibody against human MUC1 protein. Here, the antigen peptide is preferably immobilized on a solid phase, for example, beads or a membrane. The antigen peptide can also be used as a competitive substance in the competitive immunoassay of human MUC1 protein. For example, in the competitive immunoassay between an anti-MUC1 antibody and human MUC1 protein as described later, the antigen peptide can be added as a competitive substance to measure the amount of the human MUC1 protein reacted with the anti-MUC1 antibody. A label may be bound to the antigen peptide to facilitate detection. For example, biotin, a radioactive label, an enzyme label, a fluorescent label, or the like may be bound.

The present invention relates to an anti-MUC1 antibody prepared using the above-described antigen peptide as an antigen. The resultant anti-MUC1 antibody can specifically react with the full-length human MUC1 protein as well as the antigen peptide used as an antigen.

The immunogen may be prepared by dissolving the antigen peptide of human MUC1 protein obtained as described above or the antigen peptide bound to a carrier protein as an antigen in buffer. If necessary, an adjuvant may be added to effectively perform immunization. Examples of the adjuvant include commercially available Freund's complete adjuvant (FCA) and Freund's incomplete adjuvant (FIA). These adjuvants may be used alone or in a mixture.

When polyclonal antibody is prepared, the immunogen may be administered to an animal such as a mammal or a bird, for example, mouse, rabbit, rat, goat, chicken, or duck. The immunization may be carried out by injection mainly into the vein, subcutis, peritoneal cavity, or footpad. The immunization interval may not be particularly limited, and immunization may be performed 1 to 5 times at several-day to several-week intervals. Thereafter, 14 to 90 days after the final immunization day, serum or yolk (for a bird) may be collected and measured for antibody titer by immunoassay, for example, enzyme-linked immunosorbent assay (ELISA), enzyme immunoassay (EIA), or radioimmunoassay (RIA) for collection on a day when the maximum antibody titer is obtained. Then, the reactivity of polyclonal antibody specific for human MUC1 protein present in the serum or yolk can be measured by the above immunoassay or the like.

Although an antiserum may be directly used for the immunoassay method, it may be preferable to use the antibody in the antiserum after purification by affinity chromatography using human MUC1 protein or the antigen peptide, protein A or protein G affinity chromatography, and the like.

When monoclonal antibody is prepared, the immunogen may be administered to an animal such as a mammal, for example, mouse, rabbit, or rat. The immunization may be carried out by injection mainly into the vein, subcutis, peritoneal cavity, or footpad. The immunization interval may not be particularly limited, and immunization may be performed 1 to 5 times at several-day to several-week intervals. Then, 14 to 90 days after the final immunization day, antibody-producing cells may be collected. Examples of antibody-producing cells include lymph node cells, spleen cells, and peripheral blood cells.

To obtain a hybridoma, antibody-producing cells will be fused with myeloma cells. The myeloma cells which can be fused with the antibody-producing cells may be a commonly available established cell line. Preferably, the cell line to be used has drug selectivity and the property of being incapable of surviving in a HAT selection medium (containing hypoxanthine, aminopterin, and thymidine) in an unfused state and capable of surviving there only in a state fused with antibody-producing cells. Examples of myeloma cells include mouse myeloma cell lines such as P3X63-Ag.8.U1 (P3U1) and NS-I.

Then, the above myeloma cells are fused with antibody-producing cells. The cell fusion may be carried out by mixing such myeloma cells with antibody-producing cells in a medium for culturing animal cells such as serum-free DMEM or RPMI-1640 medium and performing a fusion reaction in the presence of a cell fusion promoter (e.g., polyethylene glycol). The cell fusion may also be performed using a commercial cell fusion device by electroporation.

A desired hybridoma may be selected from cells after cell fusion treatment. For example, the cell suspension may be appropriately diluted with fetal bovine serum-containing RPMI-1640 medium or the like and then seeded on a microtiter plate. A selection medium (e.g., HAT medium) may be added to each well, and cell culture may be subsequently carried out by appropriately exchanging the selection medium. As a result, cells coming to grow on the order of 10 to 30 days after the start of culture in the selection medium can be obtained as a hybridoma.

The culture supernatant of the hybridoma having come to proliferate can then be screened for whether an antibody reacting with human MUC1 protein is present or not. The screening of hybridoma may be according to a conventional method, and for example, enzyme-linked immunosorbent assay (ELISA), enzyme immunoassay (EIA), radioimmunoassay (RIA), or the like may be adopted. The cloning of fused cells may be performed by a limiting dilution or the like to establish a hybridoma producing a desired monoclonal antibody.

A usual cell culture method, a peritoneal fluid-forming method, or the like may be utilized as a method for collecting the monoclonal antibody from the established hybridoma. When the purification of the antibody is required in the method for collecting the antibody, the purification may be carried out by appropriately selecting a known method such as an ammonium sulfate precipitation, ion-exchange chromatography, gel filtration, or affinity chromatography or by combining these methods.

The globulin type of a monoclonal antibody which can be used in the present invention is not particularly limited provided that it has the activity of specifically binding to human MUC1 protein, and may be any of IgG, IgM, IgA, IgE, and IgD. Of these, IgG and IgM may be preferable.

In addition, a chimeric antibody may be prepared by splicing a gene from the antibody molecule having antigen specificity to human MUC1 protein prepared as described above together with a gene from a human antibody molecule having an appropriate biological activity (Morrison et al., 1984, Proc. Natl. Acad. Sci., 81: 6851-6855; Neuberger et al., 1984, Nature, 312: 604-608; Takeda et al., 1985, Nature, 314: 452-454). A single chain antibody (U.S. Patent No. 4,946,778; Bird, 1988, Science 242: 423-426; Huston et al., 1988, Proc. Natl. Acad. Sci. USA 85: 5879-5883; Ward et al., 1989, Nature 334: 544-546), an F(ab')$_2$ fragment, an Fab fragment, or the like may be prepared using techniques known in the art. These antibody derivatives and antibody fragments shall fall within the "antibody" of the present invention provided that they retain the desired activity, that is, reactivity with human MUC1 protein.

2. Immunoassay Reagent for Human MUC1 Protein

The antibody prepared as described above can be used to detect human MUC1 protein in a sample. The detection can be carried out based on any measurement method using an antibody, that is, an immunoassay method. For example, the detection of human MUC1 protein can be performed using an immunohistochemical staining, immune electron microscopy, immunoassay (such as enzyme immunoassay (ELISA, EIA), fluorescent immunoassay, radioimmunoassay (RIA), immunochromatography, a western blott method), or the like.

The sample may not be particularly limited; examples thereof include a tissue or cell sample (tissue or cells of cancer of the stomach, duodenum, colon, pancreas, gall bladder, bile duct, bronchus, lung, or the like), and a biological fluid sample (gastric mucus, duodenal fluid, pancreatic juice, intracystic fluid of pancreatobiliary cystic tumor, bile, ascites, expectorated sputum, bronchoalveolar lavage fluid, blood, serum, blood plasma, or the like). For example, in the case of immunostaining, a tissue sample (biopsy specimen or resected specimen) or a cytodiagnosis sample may preferably be used as a sample.

In the immunoassay method of the present invention, human MUC1 protein in a sample may be bound to the antibody according to the present invention to detect the binding to detect human MUC1 protein. For the purpose of the present invention, the "detection" encompasses not only detecting the presence or absence of human MUC1 protein but also quantitatively detecting the human MUC1 protein and immunostaining the human MUC1 protein.

The immunoassay of human MUC1 protein typically comprises contacting a sample to be tested with the antibody according to the present invention and detecting the bound antibody using a technique known in the art. The "contact" means making human MUC1 protein in a sample and the antibody according to the present invention into a state capable of coming close to each other so that they can bind together, and encompasses, for example, operations such as applying an antibody-containing solution to a solid sample, immersing a solid sample in an antibody-containing solution, and mixing a liquid sample with an antibody-containing solution.

The immunoassay may be in either liquid phase or solid phase. The foimat of the immunoassay is not limited, and may be a sandwich method, a competition method, or the like in addition to a direct solid-phase method.

The antibody according to the present invention can also be histologically used for the purpose of in situ detection of human MUC1 protein as is the case with an immunohistochemical staining (e.g., an immunostaining) or immune electron microscopy. The in situ detection can be carried out by resecting a histological sample from a subject (a biopsy tissue sample, a paraffin-embedded section of tissue, or the like) and contacting the sample with a labeled antibody.

The immunoassay procedure can be performed by a known method (Ausubel, F. M. et al. (eds.), Short Protocols in Molecular Biology, Chapter 11 "Immunology" John Wiley & Sons, Inc. 1995). Alternatively, a complex of human MUC1 protein and the antibody may be separated by a known separating means (chromatography, salting-out, alcohol precipitation, an enzyme method, a solid-phase method, or the like) to detect the signal of a label.

As an example of immunoassay, for example, when solid-phase immunoassay is used, the antibody may be immobilized on a solid support or carrier (a resin plate, a membrane, beads, or the like) or the sample may be immobilized. For example, the antibody is immobilized on the solid support, and the support is washed with an appropriate buffer and then treated with a sample. Then, the solid support is subjected to the second washing using the buffer to remove the unbound antibody. The bound antibody on the solid support can be detected by a conventional means to detect the binding between the human MUC1 protein in the sample and the antibody. Alternatively, a solid sample can be treated with an antibody-containing solution and subsequently washed with a buffer to remove the unbound antibody, followed by detecting the bound antibody on the solid sample by a conventional means.

The binding activity of an antibody can be measured according to a well-known method. One skilled in the art can determine an effective and optimal measurement method for each assay depending on the type and format of the immunoassay to be adopted, the type of the label to be used, the object to be labeled, and the like.

In one embodiment of the present invention, to facilitate the detection of the reaction between the anti-MUC1 antibody of the present invention and human MUC1 protein in a sample, the antibody of the present invention may be labeled to directly detect the reaction, or a labeled secondary antibody, a biotin-avidin complex, or the like may be used for indirect detection. Examples of the label which may be used in the present invention and detection methods thereof are described below.

In the case of the enzyme immunoassay, enzymes such as peroxidase, β-galactosidase, alkaline phosphatase, glucose oxidase, acetylcholine esterase, lactate dehydrogenase or amylase may be used. An enzyme inhibitor, a coenzyme, or the like may also be used, for example. The binding between the antibody and each of the enzymes can be performed by a known method using a cross-linking agent such as glutaraldehyde or a maleimide compound.

In the case of the fluorescent immunoassay, labels such as fluorescein isothiocyanate (FITC) or tetramethylrhodamine isothiocyanate (TRITC) may be used, for example These fluorescent labels can each be bound to the antibody by a conventional technique.

In the case of the radioimmunoassay, radioactive labels such as tritium, iodine$^{125}$ or iodine$^{131}$ may be used, for example. The radioactive label can be bound to the antibody by a known method such as a chloramine-T method or the Bolton-Hunter method.

For example, when the antibody of the present invention is directly labeled with a label as described above, a sample may be contacted with the labeled antibody of the present invention to form a human MUC1-antibody complex. For quantification, the unbound labeled antibody can be separated, followed by measuring the amount of the human MUC1 protein in the sample based on the amount of the bound labeled antibody or the amount of the unbound labeled antibody.

For example, when the labeled secondary antibody is used, the antibody of the present invention may be reacted with a sample (primary reaction), followed by further reacting the resultant complex with a labeled secondary antibody (secondary reaction). The primary reaction and the secondary reaction may be performed simultaneously or in different times. The primary reaction and the secondary reaction form a human MUC1-antibody of the present invention-labeled secondary antibody complex or an antibody of the present invention- human MUC1-labeled secondary antibody complex. Then, when quantification is performed, the unbound labeled secondary antibody can be separated, followed by measuring the amount of human MUC1 protein in the sample from the amount of the bound labeled secondary antibody or the amount of the unbound labeled secondary antibody.

When the biotin-avidin complex system is utilized, a biotinylated antibody may be reacted with a sample, followed by reacting the resultant complex with labeled avidin. Because avidin can specifically bind to biotin, the signal of the label added to avidin can be detected to measure the binding between the antibody and human MUC1 protein. The label added to avidin is not particularly limited; however, an enzyme label (peroxidase, alkaline phosphatase, or the like) may be preferable, for example.

The detection of label signal can also be performed according to a method known in the art. For example, when the enzyme label is used, a substrate degraded by an enzymatic action to develop color may be added to optically measure the degradation amount of the substrate to determine the enzyme activity, which is then converted to the amount of the bound antibody to calculate the antibody amount by comparison with a standard. The substrate varies depending on the type of the enzyme to be used; for example, 3,3',5,5'-tetramethylbenzidine (TMB), diaminobenzidine (DAB), or the like can be used when peroxidase is used as an enzyme, and para-nitrophenol or the like can be used when alkaline phosphatase is used as an enzyme. The fluorescent label can be detected and quantified using, for example, a fluorescent microscope or a plate reader. When the radioactive label is used, the amount of radiation emitted by the radioactive label may be measured using a scintillation counter or the like.

The present invention also relates to an immunoassay reagent for human mucin 1 (MUC1) protein, comprising the anti-MUC1 antibody of the present invention. In the immunoassay reagent according to the present invention, the anti-MUC1 antibody may be labeled. The anti-MUC1 antibody may be in a free form, or may be immobilized on a solid support (for example, a membrane or beads).

The immunoassay reagent may contain components useful for performing the immunoassay method in addition to the anti-MUC1 antibody of the present invention. Examples of such components include a buffer for use in the immunoassay, an agent for treating a sample, a label, a competitive substance, and a secondary antibody.

The use of the immunoassay reagent according to the present invention enables the easy and simple detection of the above-described human MUC1 protein.

3. Determination of Disease or Disorder Associated with Human MUC1 Protein

The antibody of the present invention can be used in a reagent for determining a disease or a disorder associated with human MUC1 protein because it specifically reacts with the human MUC1 protein as described above. The disease or disorder associated with human MUC1 protein means a disease or disorder having the correlation between the condition of the disease or disorder and the overexpression or underexpression of the human MUC1 protein. For example, the detection of the overexpression of human MUC1 protein enables the determination of the presence of cancers, for example, in gastric cancers, papillary adenocarcinoma (pap), tubular adenocarcinoma (tub), poorly differentiated adenocarcinoma: solid type (por1), poorly differentiated adenocarcinoma: non-solid type (por2), signet-ring cell carcinoma (sig), mucinous cancer (muc), and lymph vessel invasion lesions of cancers having a special micro-papillary pattern, and also the determination of the presence of other various human cancers (pancreatic cancer, bile duct cancer, colon cancer, ovarian cancer, breast cancer, and lung cancer). Examples of other human cancers include poorly differentiated adenocarcinoma of the colon and its lymph node metastatic foci, pancreatic cancer (PDAC), and intraductal papillary mucinous neoplasm (IPMN)-intestinal type and -gastric type.

The antibody of the present invention may be useful particularly for the detection of gastric cancer cells. When used for immunostaining, the antibody of the present invention can particularly clearly stain poorly differentiated adenocarcinoma: non-solid type (por2) and/or signet-ring cell carcinoma (sig), enabling the accurate and reliable diagnosis of such diseases.

The reagent according to the present invention comprises the above-described anti-MUC1 antibody of the present invention. Thus, human MUC1 protein contained in a sample collected from a subject who is suspected to have a disease or ta disorder can be detected using the reagent according to the present invention to rapidly and simply determine the presence of the disease or disorder in the subject. The reagent for determining a disease or disorder using an immunoassay method is known, and those of ordinary skill in the art can easily select appropriate components other than the antibody. The reagent according to the present invention can also be used in any method for performing immunoassay.

EXAMPLES

The present invention is described below in further detail, referring to Examples. The present invention is not intended to be limited thereto.

Example 1

Figure 5:
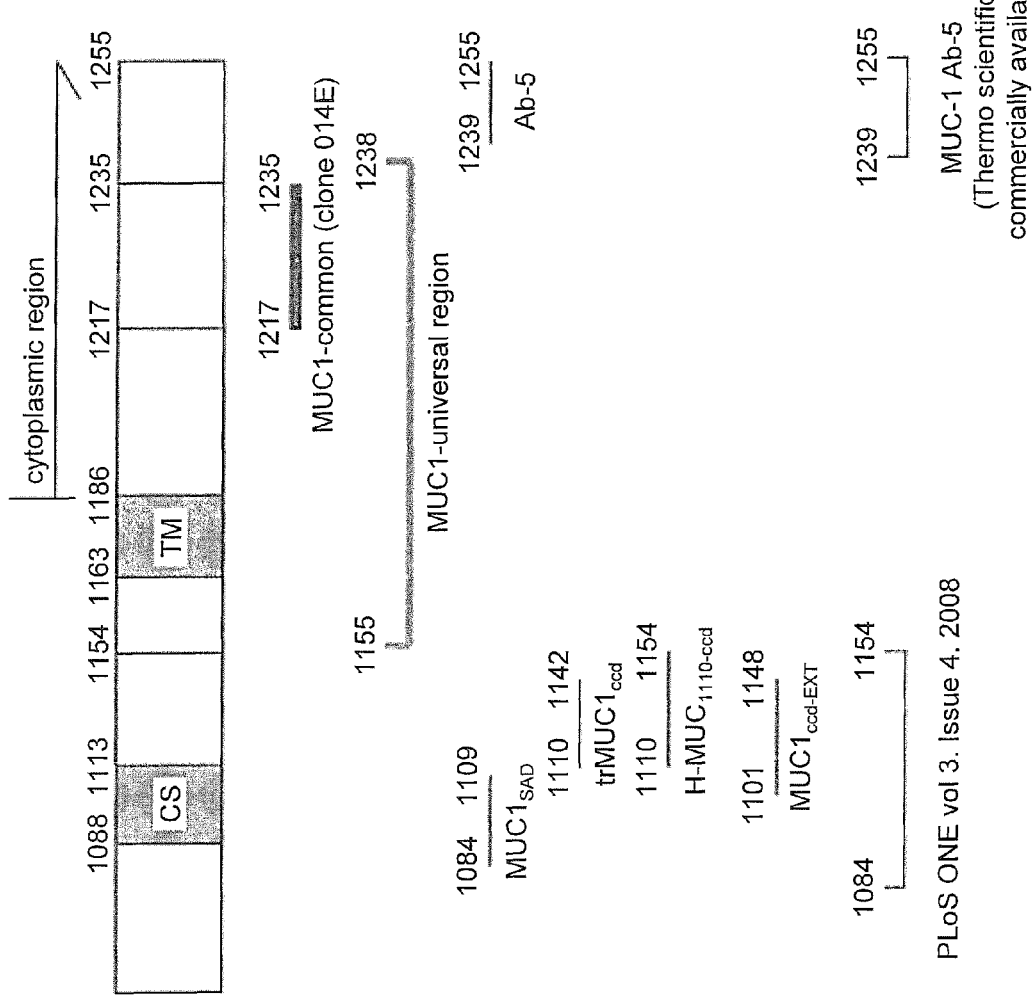
FIG. 5 shows an outline of the antigen design in human MUC1 protein.

In this Example, the selection of an epitope candidate was performed for human MUC1 protein. Specifically, the 84-amino acid region (amino acids 1,155 to 1,238: MUC1-universal region) was targeted which was located on C-terminal side of the cleavage site of human MUC1 protein and contained Region-2 to Region-5 excluding Region-1 (PLoS ONE vol. 3, Issue 4, e2054, 2008) and Region-6 (MUC1 Ab-5) against both of which antibodies had already been isolated (FIG. 5). The location of the antigens used for generating known antibodies is shown in FIG. 5.

When the 84-amino acid region as a target was subjected to the predictive analysis of B-cell epitopes based on the polarity as well as accessibility and flexibility of the constituent amino acids as parameters, 3 epitopes were selected (corresponding to Epitope No. 8 (SEQ ID NO: 19), Epitope No. 9 (SEQ ID NO: 20), and Epitope No. 10 (SEQ ID NO: 21) shown in FIGS. 2 and 3) and Region-2 in which no epitope was present was excluded.

In addition, Region-4 in which homology analysis revealed no difference between the species of human and mouse was excluded because it does not provide an immunogen as a heterologous protein, and the range of epitope candidates was narrowed to the two regions of Region-3 containing Epitope No. 8: SEQ ID NO: 19 and Region-5 containing Epitope No. 10: SEQ ID NO: 21, both of which were well conserved among human mutants (isotypes). It was finally concluded that Epitope No. 10 (STDRSPY: SEQ ID NO: 21) (FIG. 2) getting a high score in epitope analysis was the most promising, and the 19-amino acid (RYVPPSSTDRSPYEKVSAG: SEQ ID NO: 1) of Region-5 containing this epitope was used as an immunogen in Examples below (Region-5 in FIG. 4).

As described in Example 2 below, for the 45-amino acid peptide designated by "MUC1-1110-45aa" in the above Region-1 MUC1 peptide, monoclonal antibodies were also prepared using the whole 45-amino acid peptide and 15-amino acid peptides obtained by trisecting it (FIG. 4) as immunogens and preserved for comparison with a monoclonal antibody prepared using the 19-amino acid (RYVPPSSTDRSPYEKVSAG: SEQ ID NO: 1) of Region-5 as an immunogen.

Example 2

In this Example, monoclonal antibodies were prepared using MUC1 peptides as antigens.

(1) Antigen Immunization

Antigen immunization was performed as described below according to the teachings of JP Patent Publication No. 2009-284771 A. First, 7 types of MUC1 peptides (MUC1-1110_45aa-C, MUC1-1110_SPY-C, MUC1-N15-C, MUC1-MD15-C, MUC1-MD15_SPY-C, MUC1-CC-15, and MUC1-common) having the following amino acid sequences were artificially synthesized by an Fmoc solid-phase synthesis method.

Data of Amino Acid Sequence of 7 Types of MUC1 Peptides Used as Immunogen (Sequence to Which Cys for Crosslinking Is Bound)

```
(a) MUC1-1110_45aa-C
                                    (SEQ ID NO: 5)
GTINVHDVETQFNQYKTEAASRYNLITSDVSVSDVPFPFSAQSGAC (b) MUC1-1110_SPY-C
                                    (SEQ ID NO: 6)
GTINVHDVETQFNQYKTEAASPYNLTISDVSVSDVPFPFSAQSGAC (c) MUC1-N15-C
                                    (SEQ ID NO: 7)
GTINVHDVETQFNQYC (d) MUC1-MD15-C
                                    (SEQ ID NO: 8)
KTEAASRYNLTISDVC (e) MUC1-MD15_SPY-C
                                    (SEQ ID NO: 9)
KTEAASPYNLTISDVC (f) MUC1-CC-15
                                    (SEQ ID NO: 10)
CSVSDVPFPFSAQSGA (g) MUC1-common
                                    (SEQ ID NO: 11)
CRYVPPSSTDRSPYEKVSAG
```

Of the 4 peptides shown in FIG. 5, "H-MUC1 1110-ecd (the 1,110th to 1,154th amino acids of MUC1)" corresponds to "MUC1-1110_45aa-C"; however, of the 45 amino acids, the amino acid at the 22nd position from the N-terminus (the 1,131st amino acid of MUC1) is "R" as shown in FIG. 5 or SEQ ID NO: 5 in a database, while it is "P" in the description in PLoS ONE vol. 3, Issue 4, e2054, 2008.

Accordingly, the "MUC1-1110_45aa-C" (SEQ ID NO: 5) of the same 45-amino acid (the 1,110th to 1,154th amino acids of MUC1) sequence as that in the database and "MUC1-1110_SPY-C" (SEQ ID NO: 6) of the same 45-amino acid sequence as that in PLoS ONE, 2008 (supra).

The 45-amino acid sequence of the "MUC1-1110 45aa-C" was trisected, and "MUC1-N15-C" (SEQ ID NO: 7) of the N-terminal 15-amino acid sequence, "MUC1-MD15-C" (SEQ ID NO: 8) of the middle 15-amino acid sequence, and "MUC1-CC-15" (SEQ ID NO: 10) of the C-terminal 15-amino acid sequence were also prepared.

In addition, "MUC1-MD15 SPY-C" (SEQ ID NO: 9) of the middle 15-amino acid sequence in the 45-amino acid sequence of the "MUC1-1110_SPY-C" was prepared.

One milligram each of the 7 types of the partial MUC1 peptides including the MUC1-common (SEQ ID NO: 11) were weighed out, and the cysteine moiety of each peptide was cross-linked with KLH (keyhole limpet hemocyanin: Thermo) protein having a maleimide group introduced, in an aqueous solution. The resultant peptide-KLH conjugate solution (antigen solution for immunization) was mixed with an equal amount of Freund's complete adjuvant to prepare an emulsion containing 1 mg/mL of each MUC1 peptide. Two to three C57BL6 mice were provided for each peptide-KLH conjugate solution (antigen solution for immunization), and the emulsion was subcutaneously administered into the cervix thereof. The dosage was 200 μL/shot/body.

Mice were subjected to ventrotomy after 14 days of immunization, and enlarged axillary and groin lymph nodes were collected.

(2) Cell Fusion

Cells of each collected lymph node were dispersed and washed in a serum-free medium (RPMI 1640 medium), and then mixed with myeloma cells for cell fusion (P3U1) at a ratio of 5:1 (lymph node cells : myeloma cells). The cell mixture was centrifuged and the supernatant was removed to prepare a cell pellet. A 50% PEG solution prepared by dissolution in RPMI 1640 medium was added to the cell pellet at a constant rate while slightly shaking for mixing, followed by similarly adding 20 mL of RPMI 1640 medium at a constant rate for filling up to 40 mL; cell fusion was performed by this operation.

(3) HAT Selection

The fused cells obtained in (2) were suspended in 100 mL of RPMI 1640 containing 10% fetal bovine serum, and 100 μL of the suspension was dispensed into each well of ten 96-well plates. From the following day, the medium was exchanged to a medium (HAT medium) in which HAT (H: hypoxanthine, A: aminopterin, T: thymidine) was added to S-Clone cloning medium (from Sanko Junyaku Co., Ltd.) to perform culture for 10 days. In this period, medium exchange including that on the day following the day of fusion was carried out 3 times with the HAT medium. Cells having come to grow in the medium are fused cells having a de novo synthesis system and immortalized.

(4) Screening

50 μL/well each of 5 μg/mL PBS (phosphate-buffered saline) solutions of BSA-cross-linked products of 2 types of the MUC1 peptides (MUC1-1110_45aa-BSA and MUC1-common-BSA) were each independently added to an immunoplate (from Nalge Nunc), which was allowed to stand at 4° C. overnight for the physical adsorption of each peptide-BSA cross-linked product (an antigen solution for assay). The following day, after discarding the antigen solution, 50% BLOCKER™ Casein (i.e., 1% w/v casein in buffer, from Thermo) was added to 200 μL/well, which was then allowed to stand at room temperature (20 to 30° C.) for 1 hour to perform blocking operation. Thereafter, the blocking solution was discarded, and the resultant was used as an antigen plate for the following operation.

The culture supernatants (stock solution was used) in 959 of each 960 wells with the fused cell cultures obtained in (3) above were subjected to numbering and introduced into the antigen plate to perform the primary reaction at room temperature (20 to 30° C.) for 1 hour. Each well in which the reaction was completed was washed 3 times with PBS and then sufficiently drained with paper towel. An anti-mouse IgG rat monoclonal antibody cocktail-peroxidase-labeled antibody was used for the detection. 50 µL/well of a 1 µg/mL solution of the above labeled antibody was added and reacted at room temperature (20 to 30° C.) for 1 hour. Then, the labeled antibody solution was discarded, and the wells were washed 4 times with PBS. The washing liquid was sufficiently removed by striking it against paper towel, and then 50 µL/well of TMBZ [TMB One Component HRP Microwell Substrate] solution (from BIOFX) as a peroxidase substrate was introduced thereinto and color was developed at room temperature for 15 minutes. After the end of reaction, the reaction was stopped by adding an equal volume of 1 mol/L sulfuric acid, and then positive cell lines were identified with the naked eye and using a plate reader. Based on the reaction in the ten 96-well plates, wells in which absorbance at 450 nm in the plate reader was more than 2.0 were selected as strongly positive wells. 96 wells were strongly positive in the primary screening.

(5) Positive Cell Line Selection, Cloning and Cell Line Establishment

In (4), 28 hybridomas exhibiting clear positive reactions to the 7 MUC1 peptides used as immunogens could be obtained from 960 wells (containing about 10,000 colonies as cell population) to be screened. Of these, 5 cell lines having strong significance between pathology specimens and antibody reactivities (2 cell lines recognizing MUC1-N15-C (clone 14D and clone 27), 1 clone recognizing both MUC1-MD 15-C and MUC1-MD 15_SPY-C (clone 79), 1 cell line recognizing MUC1-CC-15 (clone 37A), and 1 cell line recognizing MUC1-common (clone 014E)) were found to be present by sophisticated histological screening by an immunohistostaining method using human pathological specimens. The selected 5 hybridomas were each immediately cloned by a limiting dilution method. For each of 5 completely cloned MUC1 antibody-producing hybridomas, 2 clones (the main cell line and sub-cell line) could be each assured as a master clone and a spare clone (Table 1). This means stable antibodies can be continuingly provided in the future.

TABLE 1

| Content | Cell Line No. | Epitope | Cell Storage Situation |
|---|---|---|---|
| Clone Establishment | 37A | C15 | 4 Main Cell Lines |
| | 14D | N15 | 2 Sub-Cell Lines |
| | 014E | common | (Spare Cell Stored within Company) |
| | 27 | N15 | |
| | 79 | MD15 | |

In addition, specimens of gastric cancer, pancreatic cancer, bile duct cancer, colon cancer, ovarian cancer, breast cancer and lung cancer tissues were subjected to immunohistostaining; particularly when the gastric cancer was poorly differentiated adenocarcinoma or signet-ring cell carcinoma, the monoclonal antibody "clone 014E" produced by 1 cell line recognizing MUC1-common (clone 014E) was found to be capable of clearly disclosing cancer cells of poorly differentiated adenocarcinoma or signet-ring cell carcinoma and was shown to assure the effectiveness of early diagnosis of these gastric cancers easily becoming too late. The monoclonal antibody "MUC1-common (clone 014E)" was successfully developed which can cause cancer cells of poorly differentiated adenocarcinoma or signet-ring cell carcinoma of the stomach to clearly pick out so that even a beginner having no high pathological knowledge or experience does not fail detection of these cancers which are among granulation tissue and fibrous tissue and escape detection if such a beginner simply observed a conventional HE preparation. Such reliable immunostaining of cancer cells of poorly differentiated adenocarcinoma or signet-ring cell carcinoma has a staining capability not obtained for many conventional antibodies against MUC1 or for the 4 cell lines excluding 1 cell line (clone 014E) recognizing MUC1-common, of the above 5 cell lines having the significance, now obtained by the sophisticated histological screening by an immunohistostaining method using human pathological specimens from 28 hybridomas exhibiting clear positive reactions to the 7 MUC1 peptides used as immunogens, and the monoclonal antibody "MUC1-common (clone 014E)" probably has a high merit of contributing to a histopathological diagnosis.

The hybridoma cell line obtained here was internationally deposited January 21, 2010 (original deposit) in National Insutitute of Technology and Evaluation (NITE), Patent Microorganisms Depositary (NPMD) (Department of Biotechnology, NITE, 2-5-8 Kazusakamatari, Kisarazu-shi, Chiba 292-0818, Japan) under the accession number NITE BP-867. The MUC1-common (clone 014E) is also referred to as "MUC1-014E" in the present specification and drawings.

(6) Expansion Culture of Clone

The hybridoma main cell line obtained in (5) was subjected to expansion culture in RPMI 1640 medium containing 10% fetal bovine serum, and about 250 mL of the culture supernatant was assured in refrigeration as a pure monoclonal antibody solution and could be used for immunoassay such as immunostaining as a stock solution or by partial dilution.

(7) Collection of Mouse Peritoneal fluid

Master cells of both of the main cell line and sub-cell line of each of the above hybridoma clones exhibiting reactivity to MUC1 peptide were stored as frozen cells and then, almost in parallel, the main cell line was cultured in a large amount in the abdominal cavity of scid (T and B cells deletion type) mice to provide roughly purified antibody as peritoneal fluid. The peritoneal fluid was approximately from 3 to 5 ml per mice. These were stored at −30 ° C. or lower until use.

Example 3

In this Example, polyclonal antibodies were prepared using MUC1 peptides as antigens.

Of the 7 MUC1 peptides having the amino acid sequences described in the item "(1) Antigen Immunization" of Example 2, the MUC1-common (SWQ ID NO: 11) was synthesized by an Fmoc solid-phase synthesis method.

Two milligrams of the MUC1-common peptide was weighed out and the cysteine moiety of the peptide was cross-linked with KLH (keyhole limpet hemocyanin: Thermo) protein having a maleimide group introduced, in an aqueous solution. The resultant peptide-KLH conjugate solution (antigen solution for immunization) was mixed with an equal amount of Freund's complete adjuvant: 1 mL of the antigen-cross-linked product containing 0.4 mg/mL of the MUC1-common peptide was mixed with an equal volume of FCA (Freund's complete adjuvant) to prepare an emulsion. Rabbits (KBL:JW, 17-week old, male, body weight: 3.00 kg) were each immunized by subcutaneously injecting the emulsion into the back at an antigen dose of 0.400 mg/rabbit for each immunization. After priming, the animal was boosted 3 times, followed by collecting partially collected serum through the ear vein to perform titration by ELISA. After identifying an increase in the antibody titer, the 4th and 5th boosters were effected, followed by collecting whole blood and obtaining a polyclonal antibody "MUC1-common/p."

The results of the titration using the partially collected serum showed that a polyclonal antibody having significant and sufficient binding activity at a 1:5,000 dilution could be obtained despite the serum was collected after 3 times immunization with the immune peptide. The results of ELISA are shown in Table 2.

TABLE 2

| Dilutions | day 0 | « Blood collection 2_day» | « Blood collection 3_day» | day 0 | « Blood collection 2_day» | « Blood collection 3_day» |
|---|---|---|---|---|---|---|
| $10^1$ | 0.112 | 1.285 | 1.203 | 0.085 | 0.076 | 0.090 |
| $10^2$ | 0.076 | 1.570 | 1.653 | 0.081 | 0.049 | 0.077 |
| $10^3$ | 0.069 | 1.092 | 1.294 | 0.058 | 0.068 | 0.072 |
| $10^4$ | 0.070 | 0.401 | 0.464 | 0.071 | 0.072 | 0.071 |
| $10^5$ | 0.069 | 0.124 | 0.169 | 0.067 | 0.067 | 0.068 |
| $10^6$ | 0.069 | 0.072 | 0.084 | 0.071 | 0.069 | 0.069 |
| $10^7$ | 0.068 | 0.068 | 0.070 | 0.069 | 0.067 | 0.068 |
| $10^8$ | 0.069 | 0.064 | 0.068 | 0.066 | 0.072 | 0.065 |
| | └──Antigen Coating──┘ | | | └──BLANK──┘ | | |

To further increase the purity of the resultant antiserum, antigen affinity purification was carried out using an antigen peptide-immobilized column. This resulted in the extraction of only a specific IgG from the serum, and have enabled a high-purity antibody having fairly stable reactivity to be obtained although it is a polyclonal antibody whose such reactivity is relatively prone to be dependent on the animal lot. Following the same method as that for antibody preparation now performed will reproducibly provide the polyclonal antibody "MUC1-common/p."

Example 4

In this Example, the immunostaining of gastric cancer tissue was carried out using the anti-MUC1 monoclonal antibody (MUC1-common (clone 014E)) prepared in Example 2.
(1) Immunostaining of Poorly Differentiated Adenocarcinoma Specifically, a biopsy specimen of poorly differentiated adenocarcinoma (a formalin-fixed paraffin section used for conventional pathological diagnosis) was subjected to IMBR automatic water-repellent protection treatment using a machine (Ventana XT System, Benchmark) in 10% SMEM (skim milk (Snow Brand Milk Products Co., Ltd.) dissolved in a 1:10 dilution of EZ buffer (Roche Diagnostics Co., Ltd., Code No.: 102982) to 10%) at room temperature for 12 minutes for water repellency. Then, after deparaffinization, the removal of endogenous peroxidase activity was performed for 4 minutes. Subsequently, an antigen retrieval treatment was carried out for 30 minutes using EDTA, pH 8.0. The primary antibody MUC1-common (clone 014E) (1:5 dilution) was reacted at 37° C. for 24 minutes, and an HRP-labeled anti-mouse/anti-rabbit antibody (Multimer) (Roche Diagnostics Co., Ltd., Code No.: 760-550) was further reacted for 8 minutes to bind to the primary antibody. Finally, the resultant was reacted for 8 minutes in a substrate solution in which hydrogen peroxide was mixed in DAB (diaminobenzidine) to develop color to identify the site of the antigen on the tissue section. After developing color, treatment with a color fixer for 4 minutes, hematoxylin II for 8 minutes and lithium carbonate for 4 minutes was performed using a machine to create contrast, followed by mounting (UltraView DAB research kit as a kit exclusive to the machine was used from the removal of endogenous peroxidase activity until the fixation of color development).

As controls, immunostaining with MUC1-DF3 (TFB) as a conventional anti-MUC1 antibody and hematoxylin-eosin (HE) staining were also carried out.

Specifically, the immunostaining with MUC1-DF3 was performed as follows. IMBR automatic water-repellent protection treatment using a machine (Ventana XT System, Benchmark) was carried out in 10% SMEM at room temperature for 12 minutes for water repellency. Then, after deparaffinization, the removal of endogenous peroxidase activity was performed for 4 minutes. Subsequently, an antigen retrieval treatment was carried out for 30 minutes using EDTA, pH 8.0. The primary antibody MUC1-DF3 (1:50 dilution) was reacted at 37° C. for 32 minutes, and an HRP-labeled anti-mouse/anti-rabbit antibody (Multimer) was further reacted for 8 minutes to bind to the primary antibody. Finally, the resultant was reacted for 8 minutes in a substrate solution in which hydrogen peroxide was mixed in DAB to develop color to identify the site of the antigen on the tissue section. After developing color, treatment with a color fixer for 4 minutes, hematoxylin II for 8 minutes and lithium carbonate for 4 minutes was performed using a machine to create contrast, followed by mounting (Ultra View DAB research kit as a kit exclusive to the machine was used from the removal of endogenous peroxidase activity until the fixation of color development).

HE staining was performed as follows. The specimen was first deparaffinized, washed with water, stained with Carrazzi's (2-fold) hematoxylin solution for 20 minutes, slightly washed with flowing water, placed in a 2% hydrochloric acid alcohol solution for 2 to 5 seconds for separation, washed with flowing water for about 20 to 30 minutes (color-developing), stained with an eosin staining solution for 5 minutes, dehydrated, cleared, and mounted.

Figure 6:
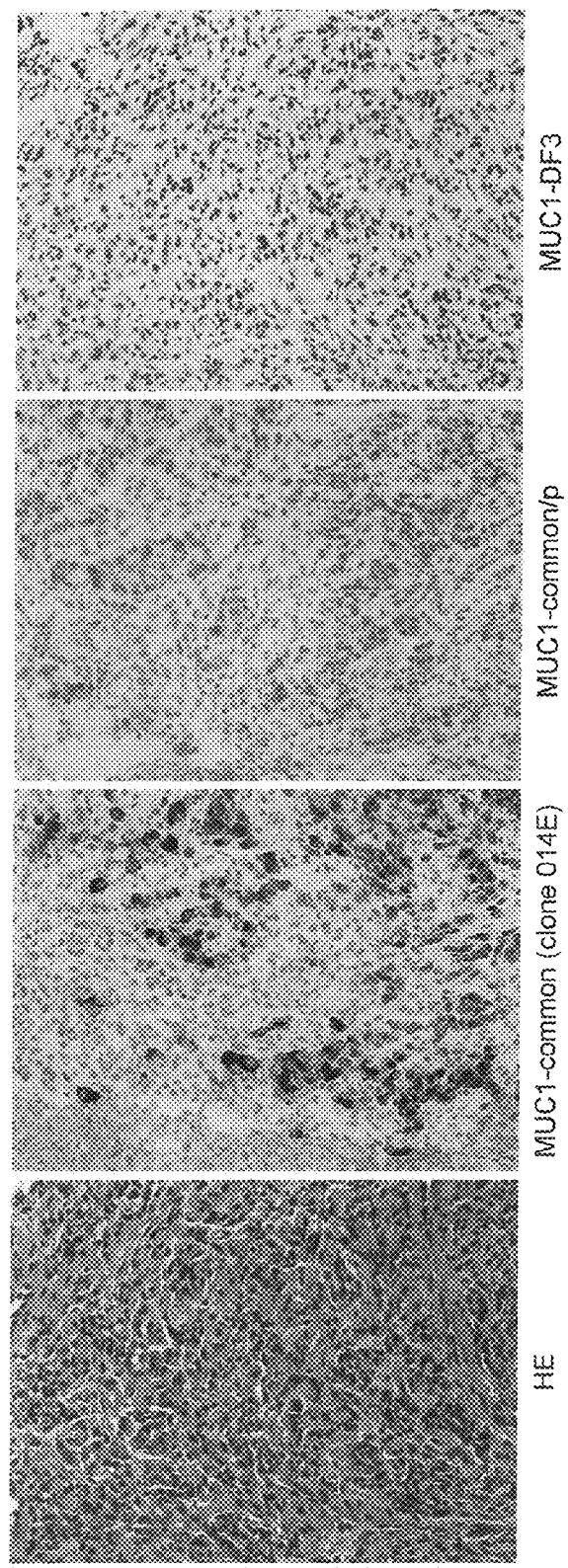
FIG. 6 is a series of photographs showing the result of immunostaining of a biopsy specimen of poorly differentiated adenocarcinoma using the anti-MUC1 antibody of the present invention.

The results are shown in FIG. 6. As shown in FIG. 6, the HE staining cannot identify the specific location of cancer cells since they are among proliferated granulation tissue and fibrous tissue, and has the risk of resulting in "misdiagnosis with cancer-detection failure." In contrast, staining with MUC1-common (clone 014E) results in only cancer cells being specifically stained and clearly appearing to pick out. When the conventional anti-MUC1 antibody (MUC1-DF3) was used, no cancer cells were stained.
(2) Comparison with Other Staining Methods Subsequently, the comparison was performed with "diastase digestion PAS" as a classical method for histochemically staining mucin and immunostainings using an antibody against another epithelial cell antigen.

In the diastase digestion PAS (D-PAS), the specimen was first deparaffinized and washed, immersed and digested at room temperature for 2 hours in a solution in which 0.2 to 0.4 g of α-amylase was dissolved in 100 ml of phosphate buffer (pH 6.5), washed with flowing water for 10 minutes, and immersed in a 2% sodium periodate solution for 10 minutes. A 10-minute washing with flowing water, a washing with distilled water, and then a 5-minute staining with Schiff reagent were carried out. After about 2-to-5-minute washing with flowing water (color-developing of such a degree that the diffusing action of dyes does not occur) and an about 5-to-10-minute nuclear staining with hematoxylin, followed by a 2-to-5-second separation using 2% hydrochloric acid alcohol and a 5-to-10-minute washing with flowing water (color-developing), it was dehydrated, cleared, and mounted.

The immunostaining using an antibody against another epithelial cell antigen was performed using an anti-MUC4 antibody clone 8G7 (a gift from Dr. Batra, Nebraska University) or 1G8 (from Invitrogen), an antibody detecting a wide range of cytokeratins, Keratin-AE1/AE3 (from Leica Biosystems Newcastle Ltd.) (30-minute retrieval treatment with EDTA, pH 8.0 and 24-minute reaction in 1:500 dilution at 37° C.) or Keratin-CAMS.2 (from Becton Japan) (30-minute antigen retrieval treatment with EDTA, pH 8.0 and 24-minute reaction in 1:25 dilution at 37° C.), an antibody against EMA (epithelial membrane antigen) (from DAKO) (no antigen retrieval, 24-minute reaction in 1:125 dilution at 37° C.), or an antibody against CEA (carcinoembryonic antigen) (from Nichirei Corporation) (no antigen retrieval, 24-minute reaction in 1:50 dilution at 37° C.) basically by the above same method as that for MUC1-common (clone 014E) or MUC1-DF3.

Figure 7:
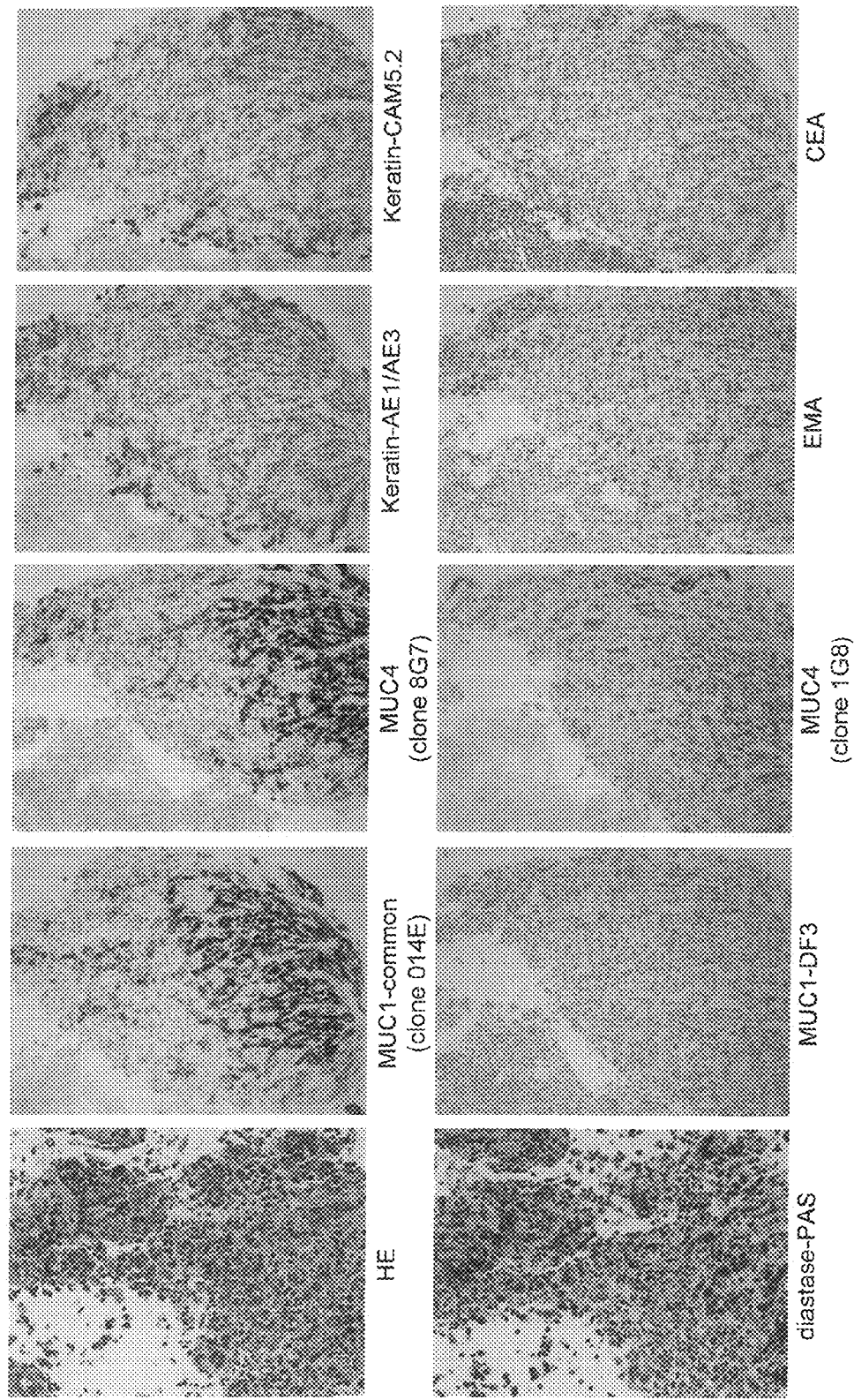
FIG. 7 is a series of photographs showing the result of immunostaining of a biopsy specimen of poorly differentiated adenocarcinoma using the anti-MUC1 antibody of the present invention together with results by other immunostaining methods.

The results are shown in FIGS. 7 to 10. As shown in FIG. 7, for poorly differentiated adenocarcinoma: non-solid type (por2), not only MUC1-common (clone 014E) but also MUC4 (clone 8G7) could detect cancer cells. Keratins (Keratin-AE1/AE3 and Keratin-CAM5.2) also strongly stained cancer cells relatively rich in cytoplasm around cancer nests. MUC4 (clone 1 G8) stained cancer cells to a degree, but could not cause cancer cells to clearly pick out since it also stained capillary vessels. Because poorly differentiated adenocarcinoma: non-solid type (por2) or signet-ring cell carcinoma is often buried in granulation tissue rich in capillary vessels, MUC4 (clone 1 G8) is not useful in detecting such cancer cells. EMA or CEA staining was positive for only a few cancer cells, and MUC1-DF3 produced no staining. The diastase digestion PAS stain as special staining also stained cancer cells of por2 to a degree, but did not stain as clearly as MUC1-common (clone 014E).

Figure 8:
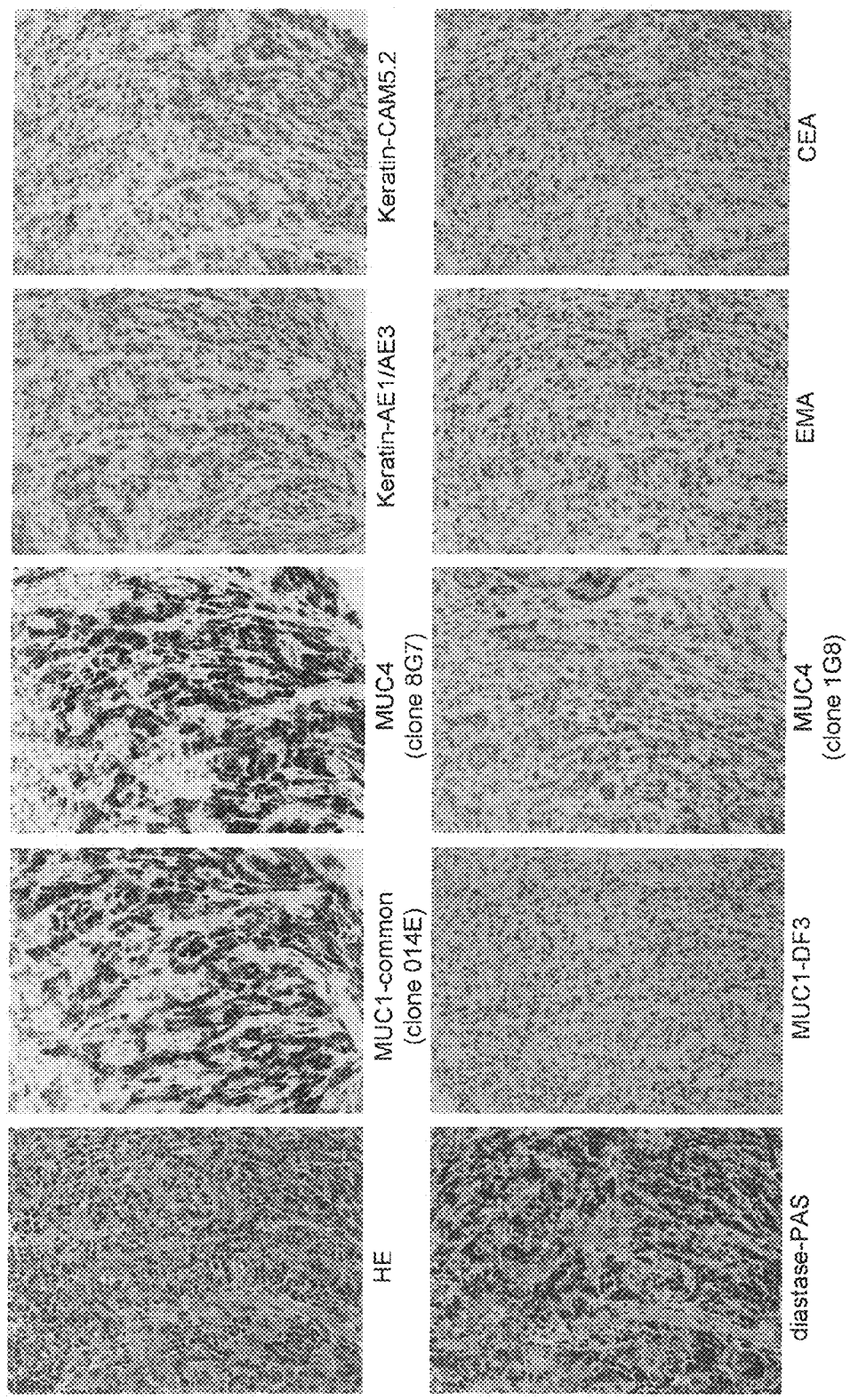
FIG. 8 is a series of photographs showing the result of immunostaining of a biopsy specimen of poorly differentiated adenocarcinoma using the anti-MUC1 antibody of the present invention together with results by other immunostaining methods.

As shown in FIG. 8, for poorly differentiated adenocarcinoma: non-solid type (por2), MUC1-common (clone 014E) and MUC4 (clone 8G7) could also detect cancer cells not rich in cytoplasm. MUC4 (clone 1G8) also stained cancer cells to a degree, but could not cause the cancer cells to pick out since it also stained capillary vessels. Keratins (Keratin-AE1/AE3 and Keratin-CAM5.2), EMA, and CEA stainings were slightly positive for cancer cells and MUC1-DF3 produced no staining. The diastase digestion PAS stain as special staining also stained cancer cells of por2, but did not stain as clearly as MUC1-common (clone 014E).

Figure 9:
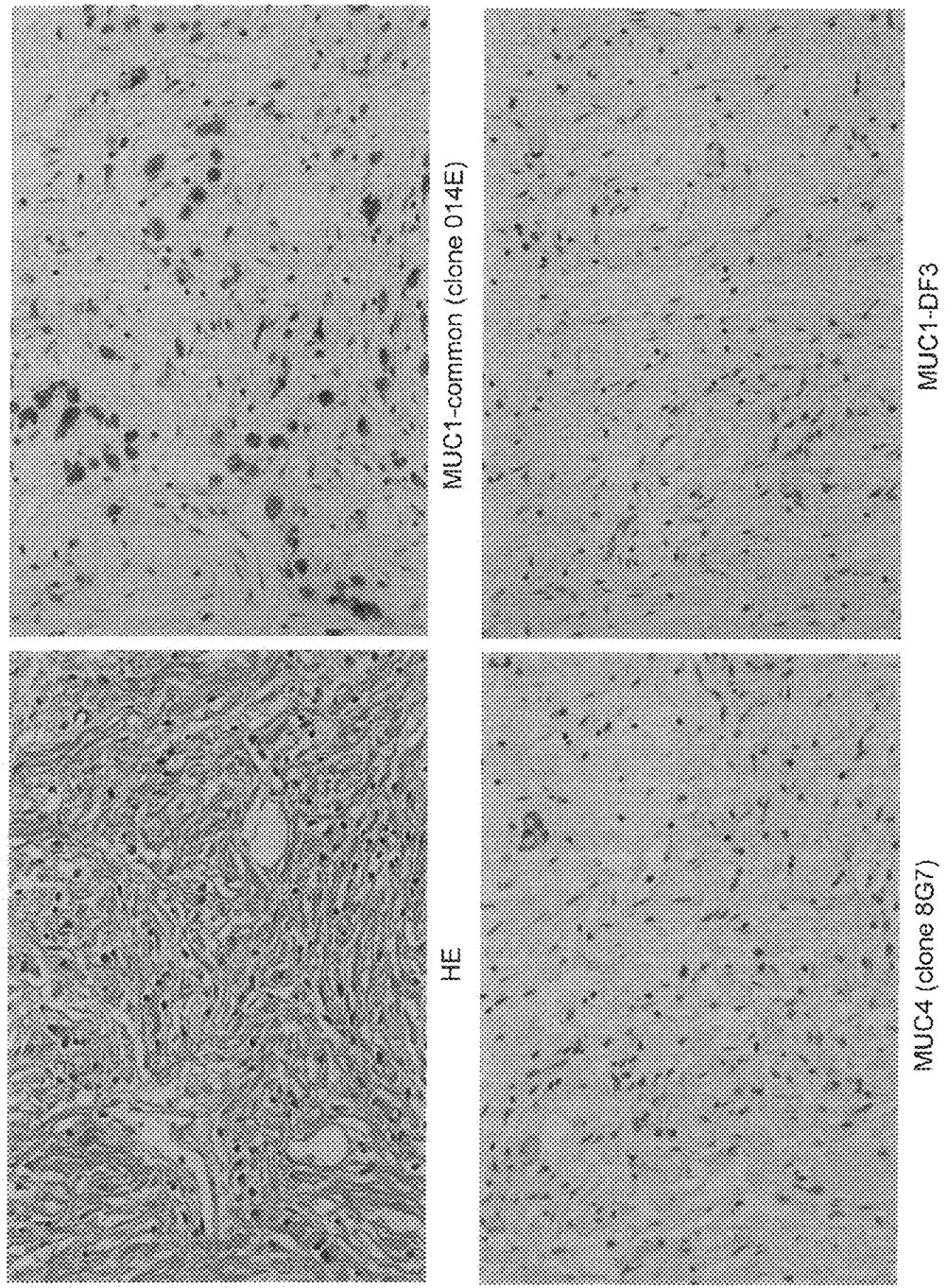
FIG. 9 is a series of photographs showing the result of immunostaining of a resected specimen of poorly differentiated adenocarcinoma using the anti-MUC1 antibody of the present invention.

As shown in FIG. 9, in another case of poorly differentiated adenocarcinoma: non-solid type (por2), only MUC1-common (clone 014E) could detect cancer cells, but MUC4 (clone 807) and MUC1-DF3 did not stain cancer cells.

Figure 10:
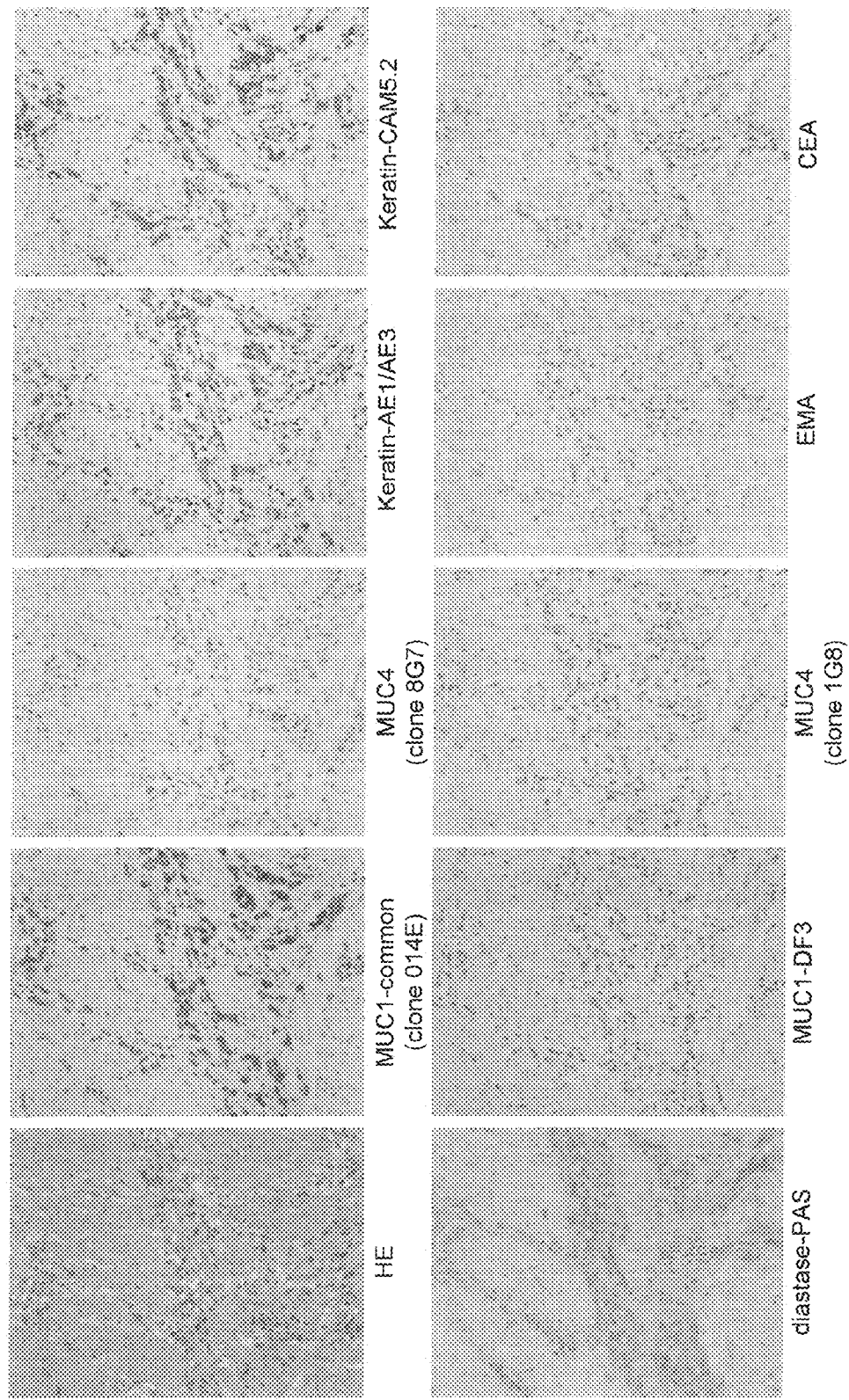
FIG. 10 is a series of photographs showing the result of immunostaining of a resected specimen of poorly differentiated adenocarcinoma using the anti-MUC1 antibody of the present invention together with results by other immunostaining methods.

FIG. 10 shows that in the site of invasion in a resected case of poorly differentiated adenocarcinoma: non-solid type (por2), MUC1-common (clone 014E) and Keratins (Keratin-AE1/AE3 and Keratin-CAM5.2) could detect cancer cells. CEA only very weakly stained a very small number of cancer cells, and MUC4 (clone 8G7), MUC4 (clone 108), EMA, and MUC1-DF3 produced no staining. The diastase digestion PAS stain as special staining stained a small number of cancer cells of por2, but did not stain as clearly as MUC1-common (clone 014E).

(3) Immunostaining of Signet-Ring Cell Carcinoma

In the same way as in (1) above, a biopsy specimen of signet-ring cell carcinoma (a formalin-fixed paraffin section used for conventional pathological diagnosis) was immunostained. The same control test as in (1) and (2) was performed.

Figure 11:
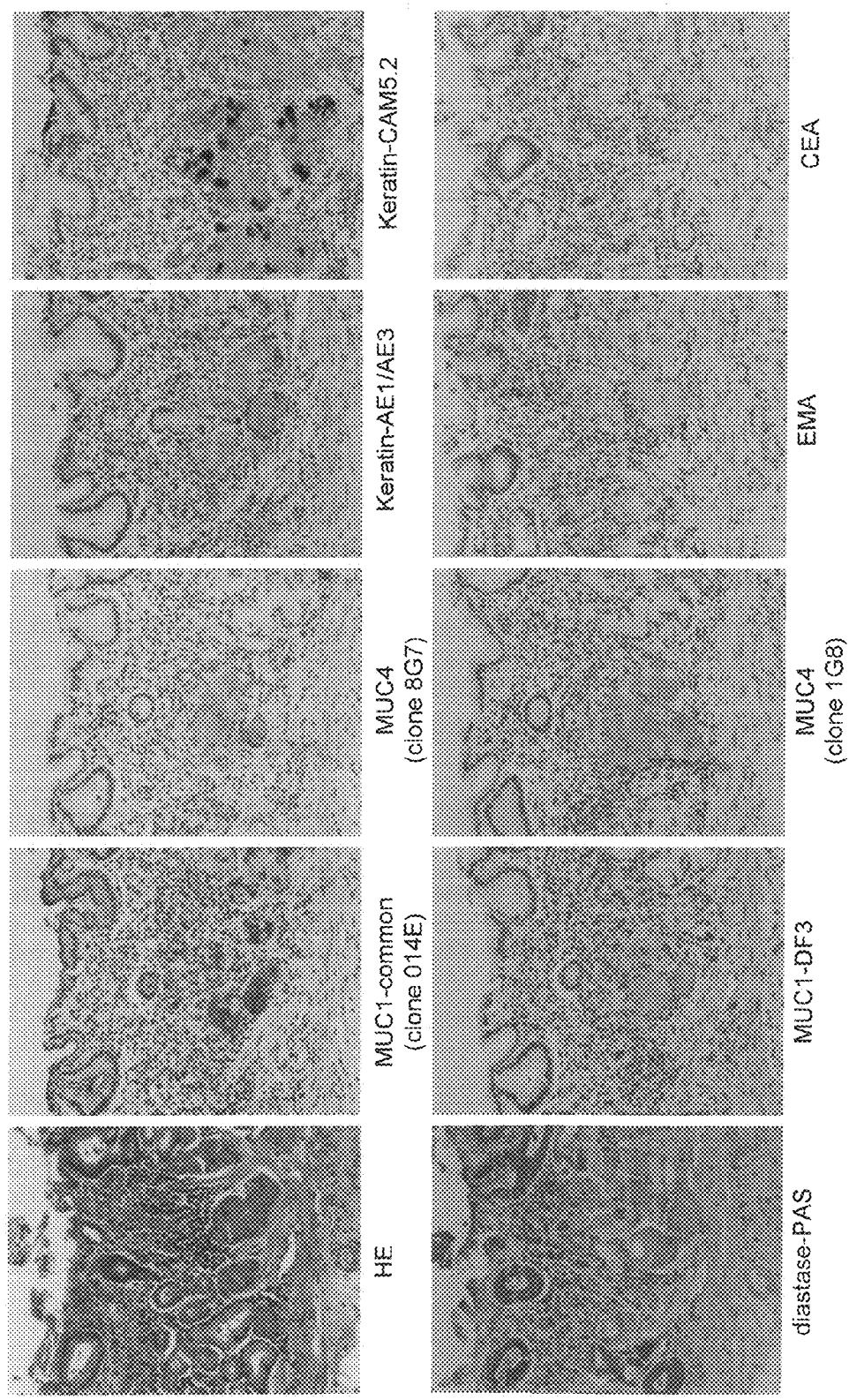
FIG. 11 is a series of photographs showing the result of immunostaining of a biopsy specimen of signet-ring cell carcinoma using the anti-MUC1 antibody of the present invention together with results by other immunostaining methods.

The results are shown in FIG. 11. For signet-ring cell carcinoma (sig), MUC1-common (clone 014E) and Keratins (Keratin-AE1/AE3 and Keratin-CAM5.2) could detect cancer cells. MUC4 (clone 1 G8) and CEA stainings were weakly positive for only a very small number of cancer cells, and MUC4 (clone 8G7), EMA, and MUC1-DF3 stained no cancer cells. Signet-ring cell carcinoma (sig) was also fairly clearly stained in the diastase digestion PAS stain as a special staining.

Example 5

In this Example, immunostainings of gastric cancer-resected specimens using anti-MUC1 antibodies were compared.

Specifically, for 59 cases of gastric cancer-resected specimens (surgically-resected specimens of early cancer in which cancer cells were less degenerated were used), immunostaining was carried out using MUC1-common (clone 014E) and MUC1-DF3. The procedure of immunostaining is the same as that in Example 4.

Two or more different histological types are often present as a mixture in gastric cancer. In fact, when classification was performed by histological type in 59 cases of gastric cancer-resected specimens now searched, there could be analyzed a total of 100 lesions (10 papillary adenocarcinoma (pap) lesions, 44 tubular adenocarcinoma (tub) lesions, 5 poorly differentiated adenocarcinoma lesions: solid type (por1), 23 poorly differentiated adenocarcinoma lesions: non-solid type (por2), 15 signet-ring cell carcinoma (sig) lesions, and 3 mucinous cancer (muc) lesions), and 3 lymph vessel invasion lesions of cancers having a special micro-papillary pattern (ly/mp).

The staining capability was evaluated based on the number of positive cells in cancer cells:
0: 0%
+/−: over 0% to under 5%
1+: more than 5% to under 25%
2+: more than 25% to under 50%
3+: more than 50% to under 75%
4+: more than 75%.

The results are shown in Table 3.

TABLE 3

| Type | Total | MUC1-common (clone 014E) | | | | | | MUC1-DF3 | | | | | |
| --- | --- | --- | --- | --- | --- | --- | --- | --- | --- | --- | --- | --- | --- |
| | | 4+ | 3+ | 2+ | 1+ | +/− | 0 | 4+ | 3+ | 2+ | 1+ | +/− | 0 |
| pap | 10 | 8 | 1 | 1 | 0 | 0 | 0 | 5 | 1 | 3 | 0 | 0 | 1 |
| tub | 44 | 40 | 0 | 2 | 0 | 1 | 1 | 5 | 3 | 7 | 9 | 8 | 12 |
| por1 | 5 | 1 | 1 | 0 | 0 | 0 | 3 | 1 | 1 | 0 | 1 | 0 | 2 |
| por2 | 23 | 23 | 0 | 0 | 0 | 0 | 0 | 0 | 0 | 0 | 0 | 0 | 23 |
| sig | 15 | 14 | 1 | 0 | 0 | 0 | 0 | 0 | 1 | 0 | 0 | 2 | 12 |
| muc | 3 | 3 | 0 | 0 | 0 | 0 | 0 | 0 | 1 | 0 | 0 | 0 | 2 |
| ly/mp* | 3 | 3 | 0 | 0 | 0 | 0 | 0 | 1 | 0 | 0 | 1 | 0 | 1 |
| | 100 | | | | | | | | | | | | |

*"ly/mp" is not contained in the total of 100 lesions.

Table 3 shows the results of immunostaining with MUC1-common (clone 014E) or MUC1-DF3 in 100 lesions of 59 gastric cancer cases. "Type" indicates the type of a lesion, and "Total" indicates the number of lesions. These results are summarized as follows.

(1) 10 Papillary Adenocarcinoma (pap) Lesions

MUC1-common (clone 014E) was 4+ in 8 lesions, 3+ in 1 lesion, and 2+ in 1 lesion among the 10 lesions. MUC1-DF3 was 4+ in 5 lesions, 3+ in 1 lesion, 2+ in 3 lesions, and 0 in 1 lesion among the 10 lesions. For both antibodies, positive findings were observed mainly in the tips of cells.

(2) 44 Tubular Adenocarcinoma (tub) Lesions

MUC1-common (clone 014E) was 4+ in 40 lesions, 2+ in 2 lesions, +/- in 1 lesion, and 0 in 1 lesion among the 44 lesions. MUC1-DF3 exhibited various degrees of positive findings of 4+ in 5 lesions, 3+ in 3 lesions, 2+ in 7 lesions, 1+ in 9 lesions, +/- in 8 lesions, and 0 in 12 lesions among the 44 lesions. For both antibodies, positive findings were observed mainly in the tips of cells.

(3) 5 Poorly Differentiated Adenocarcinoma Lesions: Solid Type (por1)

MUC1-common (clone 014E) was 4+ in 1 lesion, 3+ in 1 lesion, and 0 in 3 lesions among the 5 lesions. MUC1-DF3 was 4+ in 1 lesion, 3+ in 1 lesion, 1+ in 1 lesion, and 0 in 2 lesions among the 5 lesions. For both antibodies, positive findings were observed mainly in the cytoplasm.

(4) 23 Poorly Differentiated Adenocarcinoma Lesions: Non-Solid Type (por2)

MUC1-common (clone 014E) was 4+ in all of the 23 lesions and positive in all of the cancer cells (positive rate: 100%); the positive findings were observed in the cytoplasm. MUC1-DF3 was negative in all of the 23 lesions (positive rate: 0%).

(5) 15 Signet-Ring Cell Carcinoma (sig) Lesions

MUC1-common (clone 014E) was 4+ in 14 lesions and 3+ in 1 lesion among the 15 lesions. MUC1-DF3 was 3+ in 1 lesion, +/- in 2 lesions, and 0 in 12 lesions among the 15 lesions. For both antibodies, positive findings were observed mainly in secretion in the cytoplasm.

(6) 3 Mucinous Cancer (muc) Lesions

MUC1-common (clone 014E) was 4+ in all of the 3 lesions and positive in the cytoplasm and the cell surface in all of the cancer cells (positive rate: 100%). MUC1-DF3 was 3+ in 1 lesion, but negative in 2 lesions.

(7) Lymph Vessel Invasion Lesions of Cancers Having Special Micro-Papillary Pattern (ly/mp)

MUC1-common (clone 014E) was 4+ in the 3 lesions and positive in all of the cancer cells; positive findings in which the surface of the micro-papillary pattern was covered were obtained. MUC1-DF3 was 4+ in 1 lesion, 1+ in 1 lesion, and 0 in 1 lesion.

Summarizing the above findings, MUC1-common (clone 014E) exhibited a considerably high positive rate not only in papillary-type (pap) and tubular-type (tub) classified into "intestinal type" by Lauren's classification internationally widely known, and was positive mainly in the tips of the papillary structure and the tubular structure, but also, positive staining was observed in all cancer cells in all cases of poorly differentiated adenocarcinoma: non-solid type (por2) and in the cytoplasm of almost all cancer cells also in signet-ring cell carcinoma (sig) among poorly differentiated adenocarcinoma: solid type (por1), poorly differentiated adenocarcinoma: non-solid type (por2), and signet-ring cell carcinoma (sig) classified into "diffuse type."

Focusing on cells of "poorly differentiated adenocarcinoma: non-solid type (por2)" and "signet-ring cell carcinoma (sig)" as gastric cancer cells that would likely escape detection in a gastric biopsy tissue specimen, their biopsy specimens and resected specimens were used to perform comparison with other immunostaining and staining methods as in Example 4. The results are shown in Table 4.

TABLE 4

|  | MUC1-014E | MUC1-DF3 | MUC4 (8G7) | MUC4 (1G8) | CEA | EMA | Keratin-AE1/AE3 | Keratin-CAM5.2 |
|---|---|---|---|---|---|---|---|---|
| Biopsy Specimen | 12/12 | 1/12 | 5/12 | 1/12 | 4/12 | 5/12 | 8/12 | 10/12 |
| Resected Specimen | 10/10 | 2/10 | 2/10 | 4/10 | 4/10 | 5/10 | 8/10 | 9/10 |

The numerical values shown in Table 4 were each the ratio of the number of positive lesions of (more than 75%) to the total number of the lesions tested. MUC1-common (clone 014E) could detect gastric cancer cells in all cases in the detection of gastric cancer cells in "poorly differentiated adenocarcinoma: non-solid type (por2)" and "signet-ring cell carcinoma (sig)." Keratins (Keratin-AE1/AE3 and Keratin-CAM5.2) also stained gastric cancer cells at high rates, but the positive rates of immunostaining by other antibodies were not more than ½ times.

The immunostainings using Keratins (Keratin-AE1/AE3 and Keratin-CAM5.2), which stained "poorly differentiated adenocarcinoma: non-solid type (por2)" and "signet-ring cell carcinoma (sig)" at considerably high rates as shown in Table 4, strongly stained cancer cells relatively rich in cytoplasm around cancer nests of poorly differentiated adenocarcinoma: non-solid type (por2), but often could not clearly disclose cancer cells poor in cytoplasm in the center of cancer nests (FIG. 7) and resulted in cancer cells being wholly stained with a weak positivity (FIG. 8) as described in "(2) Comparison with Other Staining Methods" of Example 4. Thus, on the capability of staining poorly differentiated adenocarcinoma: non-solid type (por2), as clear findings as those for MUC1-common (clone 014E) were not obtained for Keratins (Keratin-AE1/AE3 and Keratin-CAM5.2), showing superiority of immunostaining with MUC1-common (clone 014E).

These findings confirm that cells of "poorly differentiated adenocarcinoma: non-solid type (por2)" and "signet-ring cell carcinoma (sig)" as gastric cancer cells that would likely escape detection in a gastric biopsy tissue specimen could be clearly detected by the antibody of the present invention. The antibody of the present invention can easily stain cancer cells of poorly differentiated adenocarcinoma: non-solid type (por2) called "scirrhous gastric cancer," which is buried in granulation tissue and fibrous tissue, and different to detect, reliably and to result in the "picking out" thereof, among other cancers, and significantly improves the reliability of the histopathological diagnosis of a gastric biopsy. The MUC1-common (clone 014E) now prepared also positively stains the normal stomach mucosa, which does not also present difficulties in differentiating cancer cells therefrom by immunostaining because the normal stomach mucosa is easy to recognize morphologically. The antibody of the present invention can also be a dominant means for detecting cancer cells of peritoneal dissemination, greatly problematical for "scirrhous gastric cancer."

Example 6

In this Example, using the anti-MUC1 polyclonal antibody "MUC1-common/p" prepared in Example 3, the immunostaining of gastric cancer tissue was performed as in Example 4. As a result, in poorly differentiated adenocarcinoma and signet-ring cell carcinoma, exactly the same results as those for the anti-MUC1 monoclonal antibody "MUC1-common (clone 014E)" were obtained ("MUC1-common/p" in FIG. 6).

Thus, having a polyclonal antibody providing exactly the same staining capability as that of a monoclonal antibody is also advantageous in the wider applications enabling the double staining (2 types of targets are stained in different colors on the same tissue by changing the secondary antibody) with another target protein.

Example 7

In this Example, immunostaining with anti-MUC1 antibodies were compared in gastric cancer- and colon cancer-resected specimens and an ascites cytodiagnosis specimen from a gastric cancer patient.

Specifically, immunostaining using MUC1 -common (clone 014E) was performed on poorly differentiated adenocarcinoma: non-solid type (por2) of the stomach, lymph node metastatic foci of poorly differentiated adenocarcinoma of the colon, and an ascites cytodiagnosis specimen of the cancerous peritonitis of a patient having the poorly differentiated adenocarcinoma of the stomach. The procedure of the immunostaining was the same as in Example 4.

Figure 13:
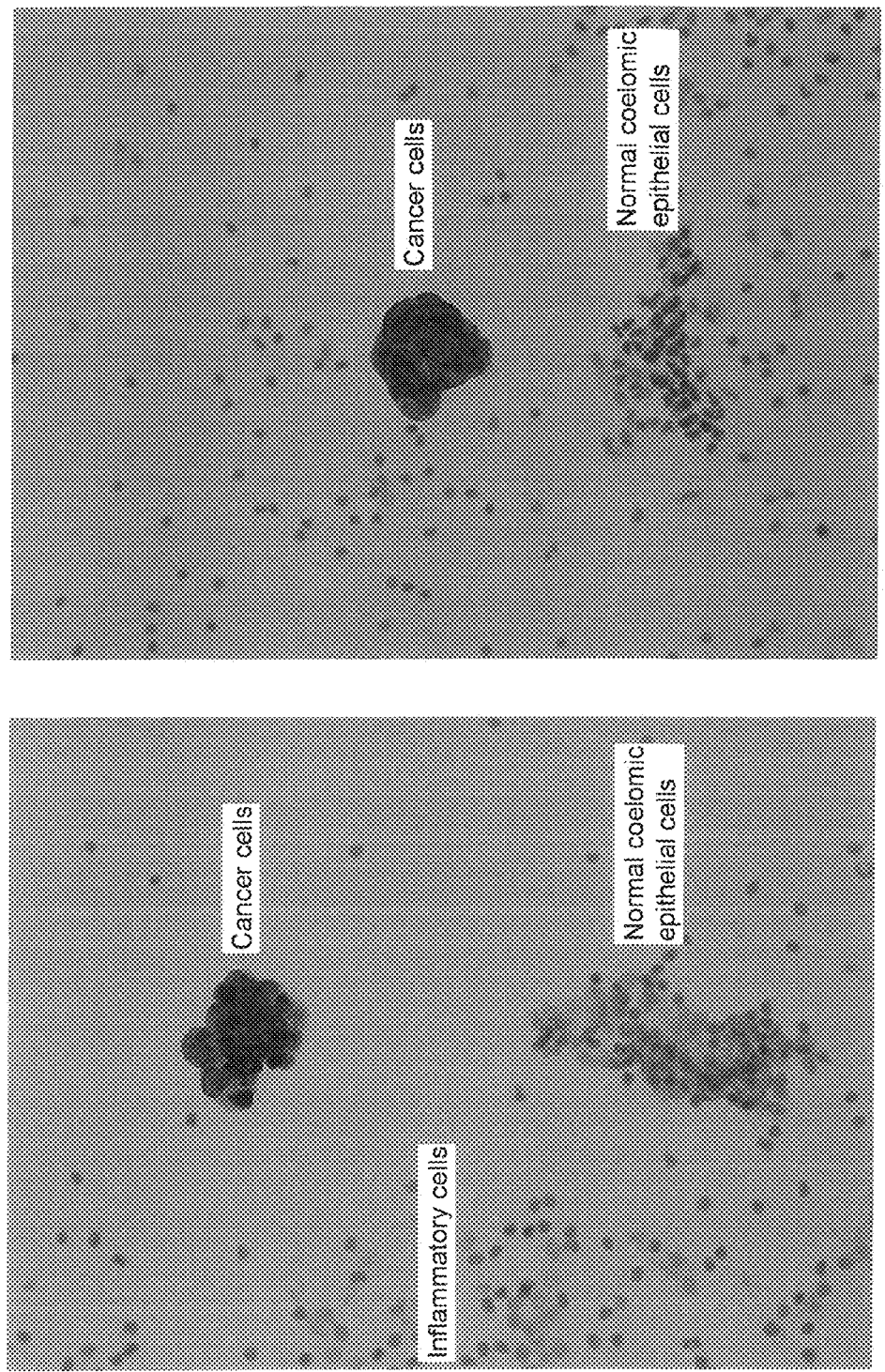
FIG. 13 are photographs showing the results of immunostaining of ascites cytodiagnosis specimens of the cancerous peritonitis of a patient having the poorly differentiated adenocarcinoma of the stomach using the anti-MUC1 antibody of the present invention.

The results are shown in FIGS. 12 and 13. In the figures, the "MUC1- 014E" means MUC1-common (clone 014E) as described above.

As shown in FIG. 12, consistent with the results of Examples 4 to 6, "MUC1-common (clone 014E)" (MUC1-014E) could immunologically stain cancer cells of poorly differentiated adenocarcinoma: non-solid type (por2) of the stomach to result in the clear "picking out" thereof (FIG. 12A).

In addition, "MUC1-014E" can immunologically stain the lymph node metastatic foci of poorly differentiated adenocarcinoma of the colon to result in the clear "picking out" thereof, and gives clearer stainability than that for Keratin-AE1/AE3 (CK-AE1/AE3) or Keratin-CAM5.2 (CK-CAM5.2) as is the case with the poorly differentiated adenocarcinoma: non-solid type (por2) (FIG. 12B). The lymph node metastatic foci of poorly differentiated adenocarcinoma of the colon were not stained by the conventional anti-MUC1 antibody "MUC1-DF3," like the poorly differentiated adenocarcinoma: non-solid type (por2) of the stomach (FIG. 12B).

As shown in FIG. 13, the immunostaining with "MUC1-014E" clearly stained cancer cells in the ascites cytodiagnosis specimen of the cancerous peritonitis of a patient having the poorly differentiated adenocarcinoma of the stomach and little stained normal coelomic epithelial cells or inflammatory cells.

As described above, the immunostaining with the anti-MUC1 antibody of the present invention can be applied to the detection of not only the primary lesion of cancer but also the metastatic foci of cancer and to the cytodiagnosis of the ascites or the pleural effusion.

Example 8

In this Example, the immunostaining with anti-MUC1 antibodies were compared in pancreatic tumor-resected specimens and normal tissue.

Specifically, pancreatic cancer (PDAC) and intraductal papillary mucinous neoplasm (IPMN)-intestinal type (IPMN-intestinal type) and -gastric type (IPMN-gastric type) were immunostained using MUC1-common (clone 014E). The procedure of the immunostaining was the same as in Example 4. The results are shown in FIG. 14.

Figure 14:
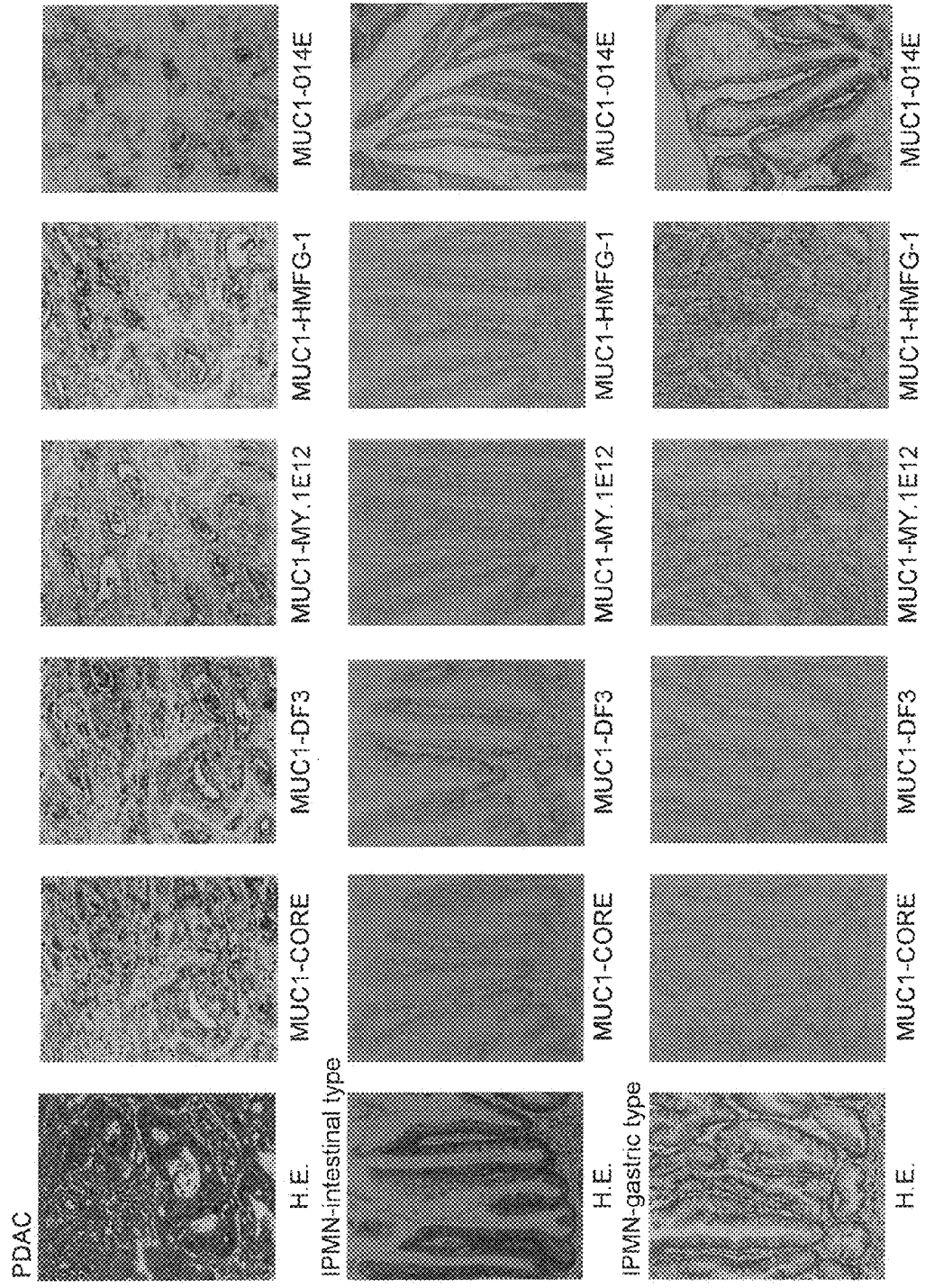
FIG. 14 is a series of photographs showing the results of immunostaining for pancreatic cancer (PDAC) and intraductal papillary mucinous neoplasm (IPMN)-intestinal type and -gastric type using the anti-MUC1 antibody of the present invention.

In FIG. 14, the "MUC1-014E" means MUC1-common (clone 014E); the "MUC1-CORE" means an antibody against the core region of human mucin 1 protein; the "MUC1-DF3" means an antibody against an antigen in which a small amount of a sugar chain is added to the core region of human mucin 1 protein; the "MUC1-MY. 1E12" means an antibody against an antigen in which a sialic acid-containing sugar chain is added to the core region of human mucin 1 protein (sialylated MUC1); and the "MUC1-HMFG-1" means an antibody against an antigen in which a long sugar chain to the end is added to the core region of human mucin 1 protein (mature-type MUC1).

The phenomenon has previously been difficult to explain in which as shown in FIG. 14, the expression states of various MUC1s are different from each other in pancreatic cancer (PDAC) and intraductal papillary mucinous neoplasm (IPMN)-intestinal type (IPMN-intestinal type) and -gastric type (IPMN-gastric type), and especially in the intraductal papillary mucinous neoplasm-gastric type (IPMN-gastric type), the sugar chain-added MUC1 s "MUC1-MY. 1E12" and "MUC1-HMFG-1" are positively stained despite "MUC1-CORE" containing no sugar chain and "MUC1-DF3" containing only a small amount of sugar chain are not stained. However, the immunostaining with "MUC1-014E" revealed that "MUC1-014E" was expressed in all of PDAC, IPMN-intestinal type, and IPMN-gastric type, which resulted in the understanding of a life phenomenon in which MUC1 itself was synthesized in all of these pancreatic tumors, enabling the explanation of the reason why the sugar chain-added MUC1 s "MUC1-MY. 1E12" and "MUC1-HMFG-1" were expressed in IPMN-gastric type.

The expression states of various MUC1s in the normal pancreatic tissue were examined by immunostaining as described above. The results are shown in FIG. 15.

The phenomenon has previously been difficult to explain in which in the normal pancreatic tissue, the area of expression of the sugar chain-added MUC1s "MUC1-MY. 1E12" and "MUC1-IIMFG-1" as shown in FIG. 15B are wider than the area of expression of "MUC1-CORE" containing no sugar chain and "MUC1-DF3" containing only a small amount of sugar chain as shown in FIG. 15A. However, "MUC1-014E" was found to be expressed in a wide area by immunostaining with "MUC1-014E," which resulted in the understanding of a life phenomenon in which MUC I itself was synthesized in a wide area of the normal pancreatic tissue, enabling the explanation of the reason why the sugar chain-added MUC1s "MUC1-MY. 1E12" and "MUC1-HMFG-1" were expressed in a wider area.

Example 9

In this Example, it was verified whether the results of DNA methylation analysis of MUC1 by the "MSE (methylation specific electrophoresis)" method in isolated duct samples of the normal mucosa and cancer tissue of the human colon showed a high correlation with the results of the immunostaining of the present invention or not.

Figure 16:
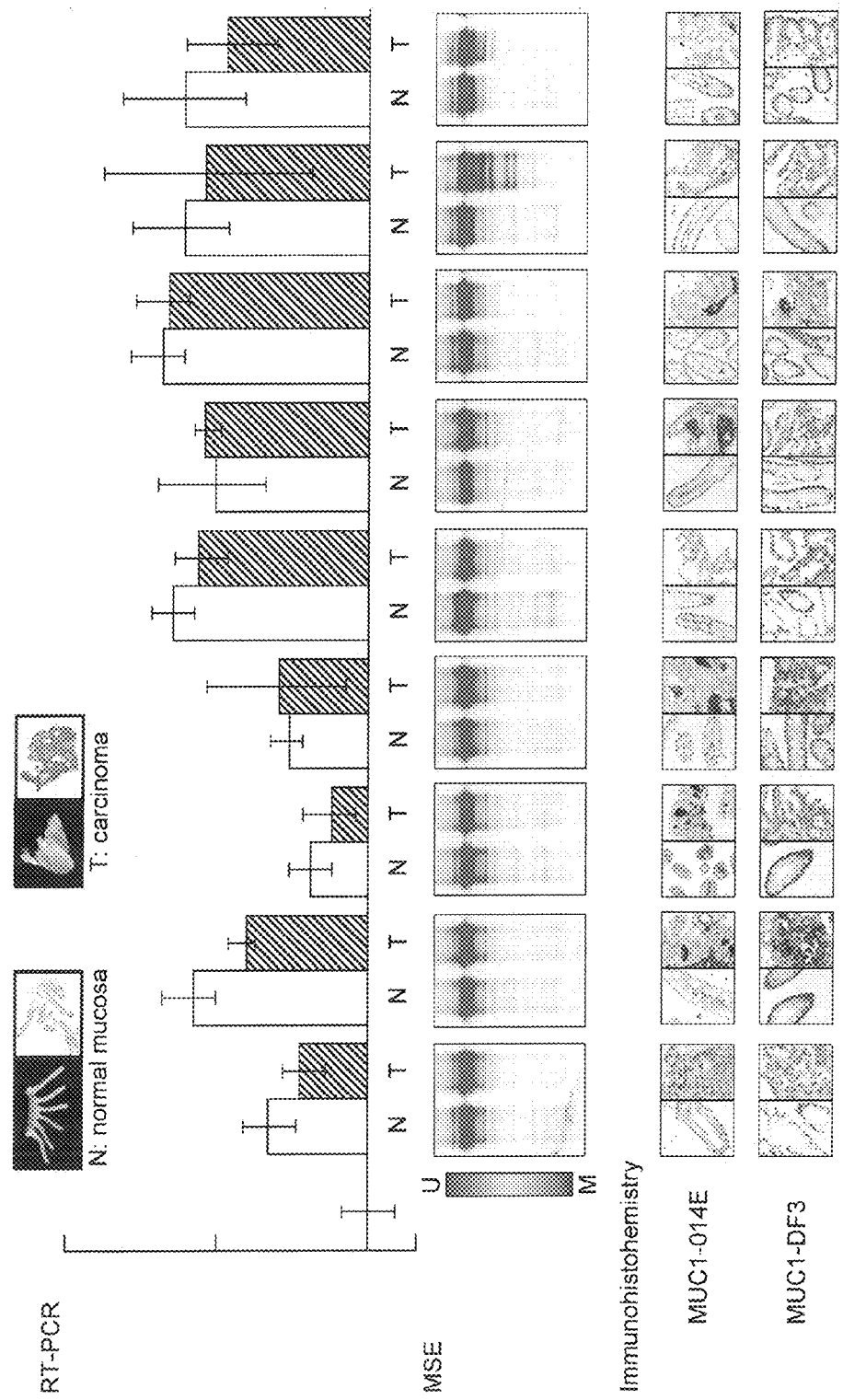
FIG. 16 shows the correlation between the results of immunostaining using the antibody of the present invention and the results of the DNA methylation analysis of MUC1 by an MSE method for isolated duct samples of the normal mucosa and cancer tissue of the human colon.

Specifically, the DNA methylation analysis of the DNA promoter region was performed by the MSE (methylation specific electrophoresis) method in the isolated duct samples of the human colon (a gift from Dr. Shinichi Nakamura and Dr. Tamotsu Sugai, Division of Pathology, lwate Medical University), in which the normal mucosa and cancer tissue of the human colon could be isolated without causing the admixture of stroma, and the results of the expression analysis of the mRNA thereof and the identification of protein expression by immunostaining were compared. The results are shown in FIG. 16.

As a result, the mRNA was found to be highly expressed in all the samples showing low methylation by the MSE method. The results did not agree with the results of immunostaining with the conventional anti-MUC1 antibody "MUC1-DF3" but showed a high correlation with the results of immunostaining with "MUC1-014E," showing that the methylation analysis of MUC1 could be performed by the MSE method in the isolated duct samples of the human colon.

Example 10

In this Example, it was confirmed whether the results of DNA methylation analysis of MUC1 by the "MSE (methylation specific electrophoresis)" method in human surgical case samples showed a correlation with the results of the immunostaining of the present invention or not.

Figure 17:
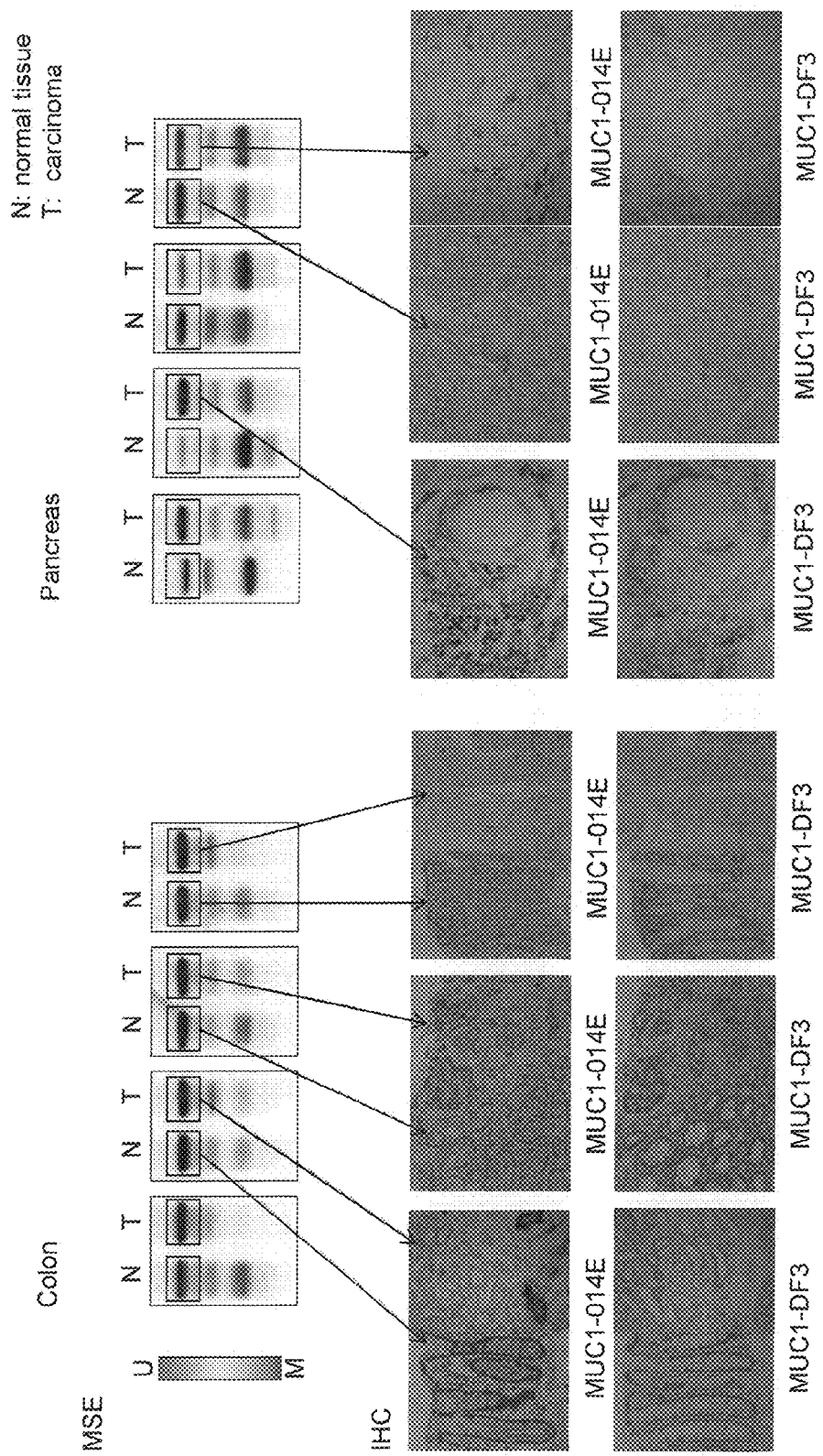
FIG. 17 shows the correlation between the results of immunostaining using the antibody of the present invention and the results of the DNA methylation analysis of MUC1 by an MSE method for human surgical case samples.

Specifically, the DNA methylation analysis of the DNA promoter region was performed by the MSE method in samples obtained from tumor and non-tumor regions of human surgical case specimens of colon cancer and pancreatic cancer, and the results of the expression analysis of the mRNA thereof and the identification of protein expression by immunostaining were compared. The results are shown in FIG. 17.

The results did not agree with the results of staining with the conventional anti-MUC1 antibody "MUC1-DF3" in all of the samples showing low methylation but also showed a high correlation with the results of immunostaining with "MUC1-014E," showing that the methylation analysis of MUC1 could be performed by the MSE method in the human surgical case samples.

Example 11

In this Example, it was confirmed whether the results of DNA methylation analysis of MUC1 by the "MSE (methylation specific electrophoresis)" method in pancreatic disease samples show a correlation with the results of the immunostaining of the present invention or not.

Figure 18:
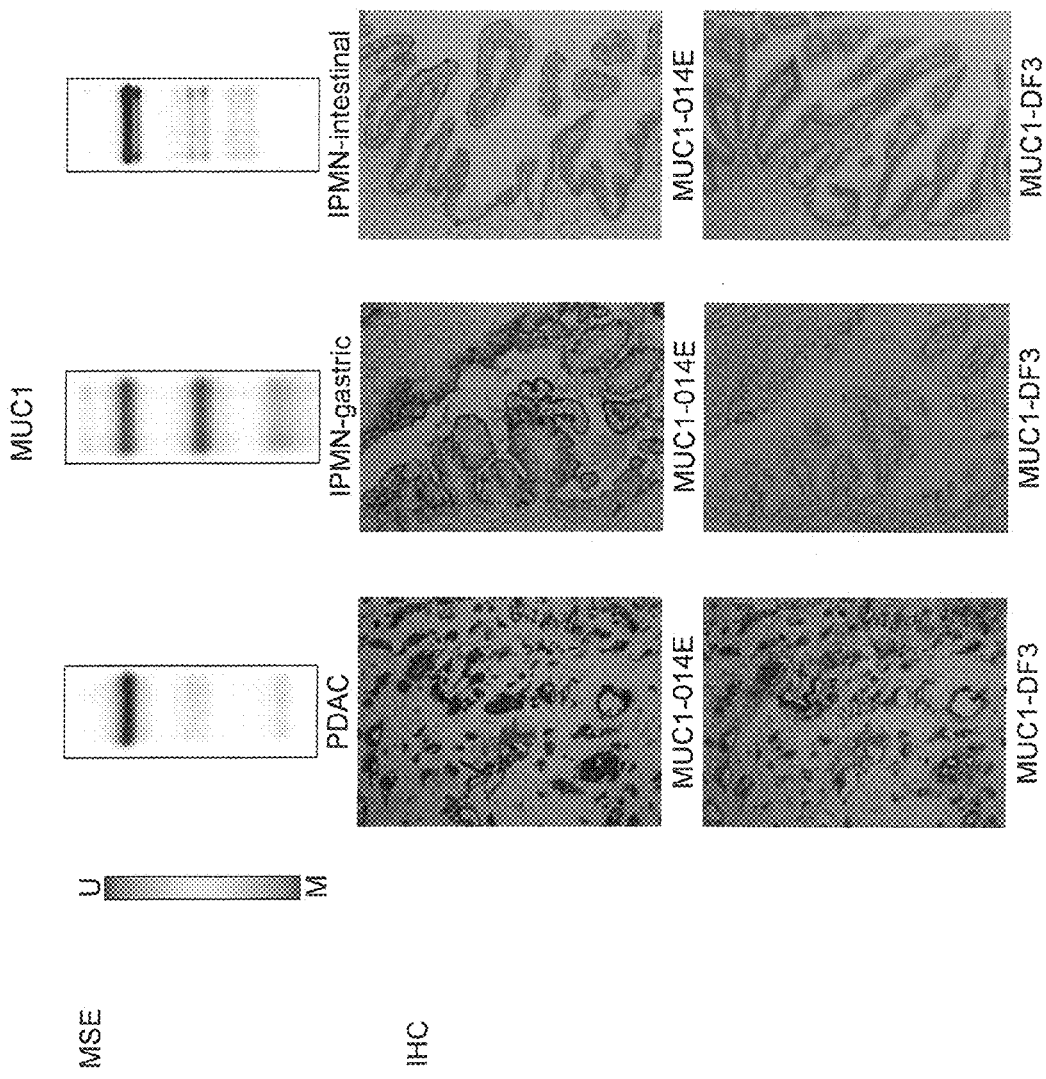
FIG. 18 shows the correlation between the results of immunostaining using the antibody of the present invention and the results of the DNA methylation analysis of MUC1 by an MSE method for human pancreatic disease samples.

Specifically, the DNA methylation analysis of the DNA promoter region of MUC1 was performed by the MSE method in samples of the pancreatic juice obtained in retrograde pancreatography from cases of human pancreatic cancer (PDAC) or intraductal papillary mucinous neoplasm-gastric type (IPMN-gastric) or the intracystic fluid of an intraductal papillary mucinous neoplasm-intestinal (IPMN-intestinal) surgical case, and the results were compared with the results of detecting the expression of the protein in the tumor tissues derived therefrom by immunostaining. The results are shown in FIG. 18.

As a result, the immunostaining with "MUC1-014E" was positive in all of the samples for which bands indicating low methylation were observed by the MSE method, and the results showed a high correlation with the results of immunostaining with "MUC1-014E" even when they did not agree with the results of immunostaining with the conventional anti-MUC1 antibody "MUC1 -DF3" (see photographs for IPMN-gastric and IPMN-intestinal). Only after the immunostaining with "MUC1-014E," it could be shown that the methylation of MU CI could be analyzed by the MSE method even in samples of the pancreatic juice and intracystic fluid of human pancreatic tumor.

All publications, patents, and patent applications cited in this application are incorporated herein by reference in their entirety.

Industrial Applicability

According to the present invention, there are provided an antibody against human mucin 1 (MUC1) protein and an antigen peptide for preparing the antibody. The use of the anti-MUC1 antibody of the present invention can sensitively, reliably, and simply detect the presence of MUC1 protein, resulting in enabling the determination of a disease or disorder associated with MIC1. The antibody may be useful in the medical diagnosis field and the pharmaceutical field.

The invention claimed is:

1. An isolated antibody that is produced by hybridoma cell line MUC1-014E, deposited as accession number NITE BP-867.

2. The isolated antibody according to claim 1, wherein the antibody is labeled.

3. A reagent for determining the presence of a cancer associated with human mucin 1 (MUC1) protein, comprising an antibody according to claim 1.

4. The reagent according to claim 3, wherein the cancer associated with human mucin 1 (MUC1) protein is selected from the group consisting of gastric cancer, pancreatic cancer, bile duct cancer, colon cancer, ovarian cancer, breast cancer, and lung cancer.

5. The reagent according to claim 4, wherein the gastric cancer is poorly differentiated adenocarcinoma or signet-ring cell carcinoma.

6. A method for determining the presence of a cancer associated with human mucin 1 (MUC1) protein in a tissue sample taken from a subject, comprising the steps of:

(a) contacting the antibody according to claim 1 with a sample from the subject; and
(b) detecting whether the antibody has bound to human mucin 1 (MUC1) protein in the sample or not;

wherein cancer is present when MUC1 is overexpressed compared to expression of MUC1 in equivalent tissue obtained from a normal control; and wherein the sample is selected from the group consisting of a biopsy tissue sample, a surgically resected tissue sample, and a cytodiagnostic sample.

7. The method according to claim 6, wherein the cancer associated with human mucin 1 (MUC1) protein is selected from the group consisting of gastric cancer, pancreatic cancer, bile duct cancer, colon cancer, ovarian cancer, breast cancer, and lung cancer.

8. The method according to claim 7, wherein the gastric cancer is poorly differentiated adenocarcinoma or signet-ring cell carcinoma.

* * * * *